(12) United States Patent
Allavatam et al.

(10) Patent No.: US 9,844,678 B2
(45) Date of Patent: Dec. 19, 2017

(54) METHODS AND DEVICES IMPLEMENTING DUAL CRITERIA FOR ARRHYTHMIA DETECTION

(71) Applicant: CAMERON HEALTH, INC., St. Paul, MN (US)

(72) Inventors: Venugopal Allavatam, Maple Grove, MN (US); Rick Sanghera, San Clemente, CA (US)

(73) Assignee: CAMERON HEALTH, INC., St. Paul, MN (US)

( * ) Notice: Subject to any disclaimer, the term of this patent is extended or adjusted under 35 U.S.C. 154(b) by 0 days.

(21) Appl. No.: 15/219,437

(22) Filed: Jul. 26, 2016

(65) Prior Publication Data

US 2016/0331985 A1 Nov. 17, 2016

Related U.S. Application Data

(63) Continuation of application No. 14/851,138, filed on Sep. 11, 2015, now Pat. No. 9,421,390, which is a
(Continued)

(51) Int. Cl.
*A61N 1/00* (2006.01)
*A61N 1/39* (2006.01)
*A61B 5/0464* (2006.01)

(52) U.S. Cl.
CPC .......... *A61N 1/3925* (2013.01); *A61B 5/0464* (2013.01); *A61N 1/3956* (2013.01); *A61N 1/3987* (2013.01)

(58) Field of Classification Search
CPC ... A61B 5/0468; A61B 5/0472; A61B 5/0452; A61B 5/7221; A61B 5/0464; A61N 1/3925; A61N 1/3956
See application file for complete search history.

(56) References Cited

U.S. PATENT DOCUMENTS 3,653,387 A 4/1972 Ceier
3,710,374 A 1/1973 Kelly
(Continued)

FOREIGN PATENT DOCUMENTS

AU 2005325670 B2 5/2012
CA 2766866 A1 1/2011
(Continued)

OTHER PUBLICATIONS

Anderson et al., "Performance of Basic Ventricular Tachycardia Detection Algorithms in Implantable Cardioverter Defibrillators: Implications for Device Programming", Pace, vol. 20 Part 1: 2975-2983, Dec 20, 1997.
(Continued)

*Primary Examiner* — Robert N Wieland
(74) *Attorney, Agent, or Firm* — Seager, Tufte & Wickhem LLP

(57) ABSTRACT

Methods and devices providing multiple criteria for use in arrhythmia identification. Based on inputs including defined rules or parameters, one of a more conservative or more aggressive set of arrhythmia identification parameters can be selected. One or the other of the selectable sets of arrhythmia identification parameters may also be adaptive or modifiable during the use of the system, for example, in response to identified nonsustained episodes, the more conservative set of arrhythmia identification parameters can be modified to become still more conservative. Such modification of arrhythmia identification criteria allows reduced time to therapy when indicated, while allowing more deliberate decisions in other circumstances.

20 Claims, 7 Drawing Sheets

Related U.S. Application Data continuation of application No. 14/203,121, filed on Mar. 10, 2014, now Pat. No. 9,149,645.

(60) Provisional application No. 61/776,326, filed on Mar. 11, 2013.

(56) References Cited

U.S. PATENT DOCUMENTS

| | | |
|---|---|---|
| 3,911,925 A | 10/1975 | Tillery, Jr. |
| 4,030,509 A | 6/1977 | Heilman et al. |
| 4,157,720 A | 6/1979 | Greatbatch |
| 4,164,946 A | 8/1979 | Langer |
| 4,184,493 A | 1/1980 | Langer et al. |
| 4,191,942 A | 3/1980 | Long |
| 4,210,149 A | 7/1980 | Heilman et al. |
| RE30,387 E | 8/1980 | Denniston, III et al. |
| 4,223,678 A | 9/1980 | Langer et al. |
| 4,248,237 A | 2/1981 | Kenny |
| 4,254,775 A | 3/1981 | Langer |
| 4,291,707 A | 9/1981 | Heilman et al. |
| 4,300,567 A | 11/1981 | Kolenik et al. |
| 4,314,095 A | 2/1982 | Moore et al. |
| 4,375,817 A | 3/1983 | Engle et al. |
| 4,402,322 A | 9/1983 | Duggan |
| 4,407,288 A | 10/1983 | Langer et al. |
| 4,424,818 A | 1/1984 | Doring et al. |
| 4,450,527 A | 5/1984 | Sramek |
| 4,457,315 A | 7/1984 | Bennish |
| 4,548,209 A | 10/1985 | Wielders et al. |
| 4,567,900 A | 2/1986 | Moore |
| 4,595,009 A | 6/1986 | Leinders |
| 4,602,637 A | 7/1986 | Elmqvist et al. |
| 4,603,705 A | 8/1986 | Speicher et al. |
| 4,679,144 A | 7/1987 | Cox et al. |
| 4,693,253 A | 9/1987 | Adams |
| 4,727,877 A | 3/1988 | Kallok |
| 4,750,494 A | 6/1988 | King |
| 4,765,341 A | 8/1988 | Mower et al. |
| 4,768,512 A | 9/1988 | Imran |
| 4,779,617 A | 10/1988 | Whigham |
| 4,800,883 A | 1/1989 | Winstrom |
| 4,830,005 A | 5/1989 | Woskow |
| 4,830,006 A | 5/1989 | Haluska et al. |
| 4,880,005 A | 11/1989 | Pless et al. |
| 4,940,054 A | 7/1990 | Grevis et al. |
| 4,944,300 A | 7/1990 | Saksena |
| 4,949,719 A | 8/1990 | Pless et al. |
| 4,979,110 A | 12/1990 | Albrecht et al. |
| 4,989,602 A | 2/1991 | Sholder et al. |
| 5,000,189 A | 3/1991 | Throne et al. |
| 5,044,374 A | 9/1991 | Lindemans et al. |
| 5,105,810 A | 4/1992 | Collins et al. |
| 5,105,826 A | 4/1992 | Smits et al. |
| 5,109,842 A | 5/1992 | Adinolfi |
| 5,117,824 A | 6/1992 | Keimel et al. |
| 5,129,392 A | 7/1992 | Bardy et al. |
| 5,133,353 A | 7/1992 | Hauser |
| 5,144,946 A | 9/1992 | Weinberg et al. |
| 5,179,945 A | 1/1993 | Van Hofwegen et al. |
| 5,184,615 A | 2/1993 | Nappholz et al. |
| 5,184,616 A | 2/1993 | Weiss |
| 5,188,105 A | 2/1993 | Keimel |
| 5,190,034 A | 3/1993 | Sholder |
| 5,191,884 A | 3/1993 | Gilli et al. |
| 5,191,901 A | 3/1993 | Dahl et al. |
| 5,193,535 A | 3/1993 | Bardy et al. |
| 5,203,348 A | 4/1993 | Dahl et al. |
| 5,215,081 A | 6/1993 | Ostroff |
| 5,215,098 A | 6/1993 | Steinhaus et al. |
| 5,217,021 A | 6/1993 | Steinhaus et al. |
| 5,230,337 A | 7/1993 | Dahl et al. |
| 5,251,625 A | 10/1993 | Wilson et al. |
| 5,255,692 A | 10/1993 | Neubauer et al. |
| 5,257,621 A | 11/1993 | Bardy et al. |
| 5,261,400 A | 11/1993 | Bardy |
| 5,271,411 A | 12/1993 | Ripley et al. |
| 5,275,621 A | 1/1994 | Mehra |
| 5,277,190 A | 1/1994 | Moulton |
| 5,280,792 A | 1/1994 | Leong et al. |
| 5,299,119 A | 3/1994 | Kraf et al. |
| 5,300,106 A | 4/1994 | Dahl et al. |
| 5,312,441 A | 5/1994 | Mader et al. |
| 5,313,953 A | 5/1994 | Yomtov et al. |
| 5,330,504 A | 7/1994 | Somerville et al. |
| 5,331,966 A | 7/1994 | Bennett et al. |
| 5,342,402 A | 8/1994 | Olson et al. |
| 5,342,407 A | 8/1994 | Dahl et al. |
| 5,351,686 A | 10/1994 | Steuer et al. |
| 5,351,696 A | 10/1994 | Riff et al. |
| 5,354,316 A | 10/1994 | Keimel |
| 5,366,496 A | 11/1994 | Dahl et al. |
| 5,370,667 A | 12/1994 | Alt |
| 5,376,103 A | 12/1994 | Anderson et al. |
| 5,376,104 A | 12/1994 | Sakai et al. |
| 5,385,574 A | 1/1995 | Hauser et al. |
| 5,391,200 A | 2/1995 | KenKnight et al. |
| 5,405,363 A | 4/1995 | Kroll et al. |
| 5,411,031 A | 5/1995 | Yomtov |
| 5,411,539 A | 5/1995 | Neisz |
| 5,411,547 A | 5/1995 | Causey, III |
| 5,413,591 A | 5/1995 | Knoll |
| 5,423,326 A | 6/1995 | Wang et al. |
| 5,431,693 A | 7/1995 | Schroeppel |
| 5,439,485 A | 8/1995 | Mar et al. |
| 5,447,519 A | 9/1995 | Peterson |
| 5,447,521 A | 9/1995 | Anderson et al. |
| 5,458,623 A | 10/1995 | Lu et al. |
| 5,464,430 A | 11/1995 | Rossing |
| 5,464,431 A | 11/1995 | Adams et al. |
| 5,476,503 A | 12/1995 | Yang |
| 5,509,923 A | 4/1996 | Middleman et al. |
| 5,509,928 A | 4/1996 | Acken |
| 5,513,645 A | 5/1996 | Jacobson et al. |
| 5,522,852 A | 6/1996 | White et al. |
| 5,531,765 A | 7/1996 | Pless |
| 5,531,766 A | 7/1996 | Kroll et al. |
| 5,534,019 A | 7/1996 | Paspa |
| 5,534,022 A | 7/1996 | Hoffmann et al. |
| 5,545,186 A | 8/1996 | Olson et al. |
| 5,558,098 A | 9/1996 | Fain |
| 5,597,956 A | 1/1997 | Ito et al. |
| 5,601,607 A | 2/1997 | Adams |
| 5,603,732 A | 2/1997 | Dahl et al. |
| 5,607,455 A | 3/1997 | Armstrong |
| 5,618,287 A | 4/1997 | Fogarty et al. |
| 5,620,477 A | 4/1997 | Pless et al. |
| 5,643,328 A | 7/1997 | Cooke et al. |
| 5,645,586 A | 7/1997 | Meltzer |
| 5,658,317 A | 8/1997 | Haefner et al. |
| 5,658,319 A | 8/1997 | Kroll |
| 5,658,321 A | 8/1997 | Fayram et al. |
| 5,674,260 A | 10/1997 | Weinberg |
| 5,690,648 A | 11/1997 | Fogarty et al. |
| 5,690,683 A | 11/1997 | Haefner et al. |
| 5,697,953 A | 12/1997 | Kroll et al. |
| 5,709,215 A | 1/1998 | Perttu et al. |
| 5,713,926 A | 2/1998 | Hauser et al. |
| 5,755,736 A | 5/1998 | Gillberg et al. |
| 5,766,225 A | 6/1998 | Kramm |
| 5,766,226 A | 6/1998 | Pedersen |
| 5,776,169 A | 7/1998 | Schroeppel |
| 5,779,645 A | 7/1998 | Olson et al. |
| 5,792,192 A | 8/1998 | Lu |
| 5,814,090 A | 9/1998 | Latterell et al. |
| 5,817,134 A | 10/1998 | Greenhut et al. |
| 5,827,197 A | 10/1998 | Bocek et al. |
| 5,827,326 A | 10/1998 | Kroll et al. |
| 5,836,975 A | 11/1998 | DeGroot |
| 5,836,976 A | 11/1998 | Min et al. |
| 5,843,132 A | 12/1998 | Ilvento |
| 5,857,977 A | 1/1999 | Caswell et al. |
| 5,895,414 A | 4/1999 | Sanchez-Zambrano |
| 5,904,705 A | 5/1999 | Kroll et al. |
| 5,919,211 A | 7/1999 | Adams |

(56) References Cited

U.S. PATENT DOCUMENTS

| | | |
|---|---|---|
| 5,919,222 A | 7/1999 | Hjelle et al. |
| 5,925,069 A | 7/1999 | Graves et al. |
| 5,935,154 A | 8/1999 | Westlund |
| 5,941,831 A | 8/1999 | Turcott |
| 5,941,904 A | 8/1999 | Johnston et al. |
| 5,957,956 A | 9/1999 | Kroll et al. |
| 5,991,657 A | 11/1999 | Kim |
| 6,014,586 A | 1/2000 | Weinberg et al. |
| 6,026,325 A | 2/2000 | Weinberg et al. |
| 6,041,251 A | 3/2000 | Kim et al. |
| 6,047,210 A | 4/2000 | Kim et al. |
| 6,052,617 A | 4/2000 | Kim |
| 6,058,328 A | 5/2000 | Levine et al. |
| 6,061,592 A | 5/2000 | Nigam |
| 6,093,173 A | 7/2000 | Balceta et al. |
| 6,095,987 A | 8/2000 | Shmulewitz et al. |
| 6,115,628 A | 9/2000 | Stadler et al. |
| H0001905 H | 10/2000 | Hill |
| 6,128,531 A | 10/2000 | Campbell-Smith |
| 6,144,866 A | 11/2000 | Miesel et al. |
| 6,144,879 A | 11/2000 | Gray |
| 6,148,230 A | 11/2000 | Kenknight |
| 6,169,923 B1 | 1/2001 | Kroll |
| 6,185,450 B1 | 2/2001 | Seguine et al. |
| 6,223,078 B1 | 4/2001 | Marcovecchio |
| 6,230,055 B1 | 5/2001 | Sun et al. |
| 6,236,882 B1 | 5/2001 | Lee et al. |
| 6,240,313 B1 | 5/2001 | Esler |
| 6,266,554 B1 | 7/2001 | Hsu et al. |
| 6,266,567 B1 | 7/2001 | Ishikawa et al. |
| 6,272,377 B1 | 8/2001 | Sweeney et al. |
| 6,278,894 B1 | 8/2001 | Salo et al. |
| 6,280,462 B1 | 8/2001 | Hauser et al. |
| 6,308,095 B1 | 10/2001 | Hsu et al. |
| 6,334,071 B1 | 12/2001 | Lu |
| 6,345,198 B1 | 2/2002 | Mouchawar et al. |
| 6,377,844 B1 | 4/2002 | Graen |
| 6,381,493 B1 | 4/2002 | Stadler et al. |
| 6,393,316 B1 | 5/2002 | Gillberg et al. |
| 6,397,100 B2 | 5/2002 | Stadler et al. |
| 6,411,844 B1 | 6/2002 | Kroll et al. |
| 6,438,410 B2 | 8/2002 | Hsu et al. |
| 6,445,949 B1 | 9/2002 | Kroll |
| 6,449,503 B1 | 9/2002 | Hsu |
| 6,487,443 B2 | 11/2002 | Olson et al. |
| 6,493,579 B1 | 12/2002 | Gilkerson et al. |
| 6,493,584 B1 | 12/2002 | Lu |
| 6,499,503 B2 | 12/2002 | Coscarella |
| 6,505,068 B2 | 1/2003 | Bonnet et al. |
| 6,516,225 B1 | 2/2003 | Florio |
| 6,539,257 B1 | 3/2003 | KenKnight |
| 6,561,984 B1 | 5/2003 | Turcott |
| 6,567,691 B1 | 5/2003 | Stadler |
| 6,574,505 B1 | 6/2003 | Warren |
| 6,575,912 B1 | 6/2003 | Turcott |
| 6,587,720 B2 | 7/2003 | Hsu et al. |
| 6,587,723 B1 | 7/2003 | Sloman et al. |
| 6,625,490 B1 | 9/2003 | McClure et al. |
| 6,636,762 B2 | 10/2003 | Begemann |
| 6,636,764 B1 | 10/2003 | Fain et al. |
| 6,643,549 B1 | 11/2003 | Bradley et al. |
| 6,647,292 B1 | 11/2003 | Bardy et al. |
| 6,658,293 B2 | 12/2003 | Vonk |
| 6,684,100 B1 | 1/2004 | Sweeney et al. |
| 6,687,540 B2 | 2/2004 | Marcovecchio |
| 6,699,200 B2 | 3/2004 | Cao et al. |
| 6,708,058 B2 | 3/2004 | Kim et al. |
| 6,708,062 B2 | 3/2004 | Ericksen et al. |
| 6,718,198 B2 | 4/2004 | Conley et al. |
| 6,721,597 B1 | 4/2004 | Bardy et al. |
| 6,728,572 B2 | 4/2004 | Hsu et al. |
| 6,728,575 B2 | 4/2004 | Hedberg |
| 6,731,978 B2 | 5/2004 | Olson et al. |
| 6,745,068 B2 | 6/2004 | Koyrakh et al. |
| 6,745,076 B2 | 6/2004 | Wohlgemuth et al. |
| 6,754,528 B2 | 6/2004 | Bardy et al. |
| 6,760,615 B2 | 7/2004 | Ferek-Petric |
| 6,766,190 B2 | 7/2004 | Ferek-Petric |
| 6,778,860 B2 | 8/2004 | Ostroff et al. |
| 6,788,974 B2 | 9/2004 | Bardy et al. |
| 6,834,204 B2 | 12/2004 | Ostroff et al. |
| 6,865,417 B2 | 3/2005 | Rissmann et al. |
| 6,866,044 B2 | 3/2005 | Bardy et al. |
| 6,879,856 B2 | 4/2005 | Stadler et al. |
| 6,889,079 B2 | 5/2005 | Bocek et al. |
| 6,909,916 B2 | 6/2005 | Spinelli et al. |
| 6,950,702 B2 | 9/2005 | Sweeney |
| 7,016,730 B2 | 3/2006 | Ternes |
| 7,020,523 B1 | 3/2006 | Lu et al. |
| 7,027,856 B2 | 4/2006 | Zhou et al. |
| 7,027,858 B2 | 4/2006 | Cao et al. |
| 7,027,862 B2 | 4/2006 | Dahl et al. |
| 7,031,764 B2 | 4/2006 | Schwartz et al. |
| 7,062,314 B2 | 6/2006 | Zhu et al. |
| 7,062,315 B2 | 6/2006 | Koyrakh et al. |
| 7,062,322 B2 | 6/2006 | Stadler et al. |
| 7,076,289 B2 | 7/2006 | Sarkar et al. |
| 7,085,599 B2 | 8/2006 | Kim et al. |
| 7,103,404 B2 | 9/2006 | Stadler et al. |
| 7,117,035 B2 | 10/2006 | Wagner et al. |
| 7,149,575 B2 | 12/2006 | Ostroff et al. |
| 7,162,301 B2 | 1/2007 | Kim et al. |
| 7,167,747 B2 | 1/2007 | Gunderson et al. |
| 7,184,815 B2 | 2/2007 | Kim et al. |
| 7,184,818 B2 | 2/2007 | Kim et al. |
| 7,191,004 B2 | 3/2007 | Kim et al. |
| 7,194,302 B2 | 3/2007 | Bardy et al. |
| 7,218,966 B2 | 5/2007 | Haefner |
| 7,236,819 B2 | 6/2007 | Brockway et al. |
| 7,248,921 B2 | 7/2007 | Palreddy et al. |
| 7,266,409 B2 | 9/2007 | Gunderson |
| 7,283,863 B2 | 10/2007 | Gunderson et al. |
| 7,302,294 B2 | 11/2007 | Kamath et al. |
| 7,330,757 B2 | 2/2008 | Ostroff et al. |
| 7,346,392 B2 | 3/2008 | Kenknight |
| 7,376,458 B2 | 5/2008 | Palreddy et al. |
| 7,379,772 B2 | 5/2008 | Bardy et al. |
| 7,386,342 B1 | 6/2008 | Falkenberg et al. |
| 7,392,085 B2 | 6/2008 | Warren et al. |
| 7,444,182 B2 | 10/2008 | Ostroff et al. |
| 7,447,540 B1 | 11/2008 | Nabutovsky et al. |
| 7,447,544 B1 | 11/2008 | Kroll |
| 7,467,009 B2 | 12/2008 | Palreddy et al. |
| 7,477,935 B2 | 1/2009 | Palreddy et al. |
| 7,496,408 B2 | 2/2009 | Ghanem et al. |
| 7,496,409 B2 | 2/2009 | Greenhut et al. |
| 7,499,750 B2 | 3/2009 | Haefner et al. |
| 7,522,959 B2 | 4/2009 | Hauser et al. |
| 7,546,159 B1 | 6/2009 | Nabutovsky et al. |
| 7,555,335 B2 | 6/2009 | Kamath et al. |
| 7,559,900 B2 | 7/2009 | Gillberg |
| 7,567,835 B2 | 7/2009 | Gunderson et al. |
| 7,570,997 B2 | 8/2009 | Lovett et al. |
| 7,593,771 B2 | 9/2009 | Yonce et al. |
| 7,623,913 B2 | 11/2009 | Phillips |
| 7,623,916 B2 | 11/2009 | Julian |
| 7,655,014 B2 | 2/2010 | Ko et al. |
| 7,682,316 B2 | 3/2010 | Anderson et al. |
| 7,684,864 B2 | 3/2010 | Olson et al. |
| 7,715,906 B2 | 5/2010 | Krause et al. |
| 7,734,345 B2 | 6/2010 | Cinbis |
| 7,761,142 B2 | 7/2010 | Ghanem et al. |
| 7,774,049 B2 | 8/2010 | Ghanem et al. |
| 7,783,354 B2 | 8/2010 | Gunderson |
| 7,797,036 B2 | 9/2010 | Zhang et al. |
| 7,865,233 B2 | 1/2011 | Haefner |
| 7,894,894 B2 | 2/2011 | Stadler et al. |
| 7,904,142 B2 | 3/2011 | Kim et al. |
| 7,904,153 B2 | 3/2011 | Greenhut et al. |
| 7,907,993 B2 | 3/2011 | Ghanem et al. |
| 8,160,686 B2 | 4/2012 | Allavatam et al. |
| 8,160,687 B2 | 4/2012 | Warren et al. |
| 8,160,697 B2 | 4/2012 | Warren et al. |
| 8,229,563 B2 | 7/2012 | Warren et al. |

(56) References Cited

U.S. PATENT DOCUMENTS

| | | |
|---|---|---|
| 8,244,349 B2 | 8/2012 | Sanghera et al. |
| 8,249,702 B2 | 8/2012 | Warren et al. |
| 8,265,737 B2 | 9/2012 | Warren et al. |
| 8,483,841 B2 | 7/2013 | Sanghera et al. |
| 8,494,630 B2 | 7/2013 | Palreddy et al. |
| 8,565,878 B2 | 10/2013 | Allavatam et al. |
| 8,670,826 B2 | 3/2014 | Warren et al. |
| 8,868,165 B1 | 10/2014 | Nabutovsky et al. |
| 2001/0027330 A1 | 10/2001 | Sullivan et al. |
| 2002/0188215 A1 | 12/2002 | Ferek-Petric |
| 2003/0114888 A1 | 6/2003 | Stadler et al. |
| 2003/0144700 A1 | 7/2003 | Brown et al. |
| 2004/0015197 A1 | 1/2004 | Gunderson |
| 2004/0093035 A1 | 5/2004 | Schwartz et al. |
| 2004/0171959 A1 | 9/2004 | Stadler et al. |
| 2004/0215239 A1 | 10/2004 | Favet et al. |
| 2004/0215240 A1 | 10/2004 | Lovett et al. |
| 2004/0220628 A1 | 11/2004 | Wagner |
| 2004/0230229 A1 | 11/2004 | Lovett et al. |
| 2004/0254611 A1 | 12/2004 | Palreddy et al. |
| 2004/0254613 A1 | 12/2004 | Ostroff et al. |
| 2005/0004615 A1 | 1/2005 | Sanders |
| 2005/0049644 A1 | 3/2005 | Warren et al. |
| 2005/0107838 A1 | 5/2005 | Lovett et al. |
| 2005/0131464 A1 | 6/2005 | Heinrich et al. |
| 2005/0154421 A1 | 7/2005 | Ousdigian et al. |
| 2006/0036288 A1 | 2/2006 | Bocek et al. |
| 2006/0079796 A1 | 4/2006 | Marcovecchio et al. |
| 2006/0122676 A1 | 6/2006 | Ko |
| 2006/0167502 A1 | 7/2006 | Haefner |
| 2006/0167503 A1 | 7/2006 | Warren et al. |
| 2006/0167504 A1 | 7/2006 | Warren et al. |
| 2006/0217621 A1* | 9/2006 | Kim .............. A61B 5/04525 600/509 |
| 2006/0241701 A1 | 10/2006 | Markowitz et al. |
| 2007/0032829 A1 | 2/2007 | Ostroff |
| 2007/0049975 A1 | 3/2007 | Cates et al. |
| 2007/0135847 A1 | 6/2007 | KenKnight |
| 2007/0135852 A1 | 6/2007 | Kim et al. |
| 2007/0142736 A1 | 6/2007 | Cazares et al. |
| 2007/0156190 A1 | 7/2007 | Cinbis |
| 2007/0179539 A1 | 8/2007 | Degroot et al. |
| 2007/0179540 A1 | 8/2007 | Stegemann et al. |
| 2007/0232944 A1 | 10/2007 | Ghanem et al. |
| 2007/0232945 A1 | 10/2007 | Kleckner et al. |
| 2007/0232949 A1 | 10/2007 | Stadler et al. |
| 2007/0233198 A1 | 10/2007 | Ghanem et al. |
| 2007/0276445 A1 | 11/2007 | Sanghera et al. |
| 2008/0009906 A1 | 1/2008 | Perschbacher et al. |
| 2008/0015647 A1 | 1/2008 | Palreddy et al. |
| 2008/0077030 A1 | 3/2008 | Ostroff |
| 2008/0086174 A1 | 4/2008 | Libbus et al. |
| 2008/0091242 A1 | 4/2008 | Kamath et al. |
| 2008/0132965 A1 | 6/2008 | Ostroff et al. |
| 2008/0161870 A1 | 7/2008 | Gunderson |
| 2008/0172098 A1 | 7/2008 | Gunderson |
| 2008/0183085 A1 | 7/2008 | van Oort et al. |
| 2008/0188901 A1 | 8/2008 | Sanghera et al. |
| 2008/0215110 A1 | 9/2008 | Gunderson |
| 2008/0221632 A1 | 9/2008 | Bardy |
| 2008/0228093 A1 | 9/2008 | Dong et al. |
| 2008/0243200 A1 | 10/2008 | Scinicariello et al. |
| 2008/0262559 A1 | 10/2008 | Zhang et al. |
| 2008/0275516 A1 | 11/2008 | Ghanem et al. |
| 2008/0275517 A1 | 11/2008 | Ghanem et al. |
| 2008/0275519 A1 | 11/2008 | Ghanem et al. |
| 2008/0275521 A1 | 11/2008 | Warren et al. |
| 2009/0018595 A1 | 1/2009 | Bharmi et al. |
| 2009/0036788 A1 | 2/2009 | Nabutovsky et al. |
| 2009/0043352 A1 | 2/2009 | Brooke et al. |
| 2009/0054796 A1 | 2/2009 | Sanghera et al. |
| 2009/0054938 A1 | 2/2009 | Ostroff et al. |
| 2009/0093731 A1 | 4/2009 | Palreddy et al. |
| 2009/0131998 A1 | 5/2009 | Warren et al. |
| 2009/0156957 A1 | 6/2009 | Linder et al. |
| 2009/0157128 A1 | 6/2009 | Seim et al. |
| 2009/0157132 A1 | 6/2009 | Linder et al. |
| 2009/0157137 A1 | 6/2009 | Gilkerson et al. |
| 2009/0228057 A1 | 9/2009 | Allavatam et al. |
| 2009/0240157 A1 | 9/2009 | Lian et al. |
| 2009/0240300 A1 | 9/2009 | Lian et al. |
| 2009/0259271 A1 | 10/2009 | Allavatam et al. |
| 2010/0004713 A1 | 1/2010 | Warren et al. |
| 2010/0106209 A1 | 4/2010 | Gunderson et al. |
| 2010/0312131 A1 | 12/2010 | Naware et al. |
| 2010/0331904 A1 | 12/2010 | Warren et al. |
| 2011/0098775 A1 | 4/2011 | Allavatam et al. |
| 2011/0208260 A1 | 8/2011 | Jacobson |
| 2012/0029335 A1 | 2/2012 | Sudam et al. |
| 2012/0316612 A1 | 12/2012 | Warren et al. |
| 2012/0323290 A1 | 12/2012 | Warren et al. |
| 2014/0148717 A1 | 5/2014 | Eberle et al. |

FOREIGN PATENT DOCUMENTS

| | | |
|---|---|---|
| DE | 29801807 U1 | 6/1998 |
| EP | 0095727 A1 | 12/1983 |
| EP | 0316616 A2 | 5/1989 |
| EP | 0347353 A1 | 12/1989 |
| EP | 0316616 A3 | 6/1992 |
| EP | 0518599 A2 | 12/1992 |
| EP | 0517494 A3 | 3/1993 |
| EP | 0554208 A2 | 8/1993 |
| EP | 0554208 A3 | 1/1994 |
| EP | 0586858 B1 | 3/1994 |
| EP | 0627237 A1 | 12/1994 |
| EP | 0641573 A2 | 3/1995 |
| EP | 0677301 A1 | 10/1995 |
| EP | 0517494 B1 | 9/1996 |
| EP | 0641573 A3 | 6/1997 |
| EP | 0518599 B1 | 9/1997 |
| EP | 0536873 B1 | 9/1997 |
| EP | 0917887 A1 | 5/1999 |
| EP | 0923130 A1 | 6/1999 |
| EP | 1000634 A1 | 5/2000 |
| EP | 1046409 A2 | 10/2000 |
| EP | 1046409 B1 | 8/2003 |
| EP | 2459275 A1 | 6/2012 |
| JP | 2008528103 A | 7/2008 |
| JP | 2011528238 A | 11/2011 |
| JP | 2012532633 A | 12/2012 |
| WO | 8901802 A1 | 3/1989 |
| WO | 9319809 A1 | 10/1993 |
| WO | 9729802 A2 | 8/1997 |
| WO | 9825349 A1 | 6/1998 |
| WO | 9903534 A1 | 1/1999 |
| WO | 9937362 A1 | 7/1999 |
| WO | 9953991 A1 | 10/1999 |
| WO | 0041766 A1 | 7/2000 |
| WO | 0050120 A1 | 8/2000 |
| WO | 0113993 A1 | 3/2001 |
| WO | 0143649 A1 | 6/2001 |
| WO | 0156166 A2 | 8/2001 |
| WO | 0222208 A2 | 3/2002 |
| WO | 0224275 A2 | 3/2002 |
| WO | 0224275 A3 | 5/2002 |
| WO | 0222208 A3 | 6/2002 |
| WO | 02068046 A1 | 9/2002 |
| WO | 03018121 A2 | 3/2003 |
| WO | 2004091720 A2 | 10/2004 |
| WO | 2004093974 A2 | 11/2004 |
| WO | 2004093974 A3 | 12/2004 |
| WO | 2006081027 A2 | 8/2006 |
| WO | 2008111764 A1 | 9/2008 |
| WO | 2011008550 A1 | 1/2011 |

OTHER PUBLICATIONS

Bardy et al., "Multicenter Experience with a Pectoral Unipolar Implantable Cardioverter-Defibrillator", JACC, vol. 28 (2): 400-410, Aug. 1996.

Betts et al., "Inappropriate Shock Therapy in a Heart Failure Defibrillator", Pace, vol. 24(2): 238-240, Feb. 2001.

(56) References Cited

OTHER PUBLICATIONS

Boriani et al., "Cardioverter-Defibrillator Oversensing Due to Double Counting of Ventricular Tachycardia Electrograms", International Journal of Cardiology, 66: 91-95, 1998.
Callans et al., "Unique Sensing Errors in Third-Generation Implantable Cardioverter-Defibrillators", JACC, vol. 22 (4):1135-1140, Oct. 4, 1993.
Friedman et al., "Implantable Defibrillators in Children" From Whence to Shock, Journal of Cardiovascular Electrophysiology, vol. 12(3):361-362, Mar. 2001.
Gradaus et al., "Nonthoracotomy Implantable Cardioverter Defibrillator Placement in Children: Use of Subcutaneous Array Leads and Abdominally Placed Implantable Cardioverter Defibrillators in Children", Journal of Cadiovascular Electrophysiology, vol. 12(3): 356-360, Mar. 2001.
Higgins et al. "The First Year Experience with the Dual Chamber ICD", Pace, vol. 23: 18-25, Jan. 2000.
Jais, "Pacemaker Syndrome Induced by the Mode Switching Algorithm of a DDDR Pacemaker", PACE, vol. 22, Part 1: 682-685, 1999.
Jones et al., "Considerations for Ventricular Fibrillation Detection by Implantable Cardioverter Defibrillators", American Heart Journal, vol. 127(4), Part 2: 1107-1110, Apr. 1994.
Kelly et al., "Oversensing During Ventricular Pacing in Patients with a Third-Generation Implantable Cardioverter-Defibrillator", JACC vol. 23(7): 1531-1534, Jun. 1994.
Leung et al., "Apparent Extension of the Atrioventricular Interval Due to Sensor-Based Algorithm Against Supraventricular Tachyarrhythmias", PACE, vol. 17, Part 1: 321-330, Mar. 1994.
Li et al., "The Mean Ventricular Fibrillation Cycle Length: A Potentially Useful Parameter for Prgranuning Implantable Cardioverter Defibrillators", PACE vol. 21: 1789-1794, Sep. 1998.
Mirowski et al., "Automatic Detection and Defibrillation of Lethal Arrhythmias—A New concept", JAMA, vol. 213(4): 515-616, Jul. 27, 1970.
Nair et al. "Automatic Arrhythmia Identification Using Analysis of the Atrioventricular Association", Circulation, Vol. 95 (4): 967-973, Feb. 1997.
Newman et al., "Use of Telemetry Functions in the Assessment of Implanted Antitachycardia Device Efficacy", The American Journal of Cardiology, vol. 70: 616-621, Sep. 1, 1992.
Olson et al., "Onset and Stability for Ventricular Tachyarrhythmia Detection in an Implantable Pacer-Cardioverter-Defibrillator", IEEE: 167-170, 1987.
Schaumann et al., "Enhanced Detection Criteria in Implantable Cardioverter-Defibrillators to Avoid Inappropriate Therapy", The American Journal of Cardiology,vol. 78(5A): 42-50, Sep. 12, 1996.
Schreieck et al., "Inappropriate Shock Delivery Due to Ventricular Double Detection with a Biventricular Pacing Implantable Cardioverter Defibrillator", PACE, vol. 24(7): 1154-1157, Jul. 2001.
Schuder, "Completely Implanted Defibrillator", JAMA, vol. 214(6): 1123, Nov. 9, 1970.
Schuder et al., "Experimental Ventricular Defibrillation with an Automatic and Completely Implanted System", Trans. Am. Soc. Artif. Int. Organs, vol. 16: 207-212, 1970.
Schuder et al., "Standby Implanted Defibrillators", Arch Inter. Med, vol. 127: 317. Feb. 1971.
Schuder et al., "The Role of an Engineering Oriented Medical Research Group in Developing Improved Methods & Devices for Achieving Ventricular Defibrillation: The University of Missouri Experience", PACE, vol. 16, Part 1: 95-124, Jan. 1993.
Schuder et al., Transthoracic Ventricular Defibrillation in the Dog with Truncated and Untruncated Exponential Stimuli, IEEE Trans. on Bio-Medical Engin., vol. BME-18(6): 410-415, Nov. 1971.
Schwake et al., "Komplikationen mit Sonden bei 340 Patienten mit einem implantierbaren Kardioverter/Defibrilator", Z Kardiol, vol. 88(8):559-565, 1999.
Swerdlow et al., "Advanced ICD Troubleshooting: Part 1", PACE, vol. 28: 181-186, <http://www.medscape.com/viewarticle/520588. sub.--print>, Jul. 2001.
Theuns et al., "Initial Clinical Experience with a New Arrhythmia Detection Algorithm in Dual Chamber Implantable Cardioverter Defilbrillators", Europace, vol. 3:181-186, Jul. 2001.
Throne et al., "A Comparison of Four New Time-Domain Techniques for Discriminating Monomorphic Ventricular Tachycardia from Sinus Rhythm Using Ventricular Waveform Morphology", IEEE Transaction on Biomedical Engineering , vol. 38(6):561-570, Jun. 1991.
Tietze et al., "Halbleiter-Schaltungstechnik",.COPYRGT. Spring-Verlag (Berlin, Germany),:784-786,1991.
Valenzuela et al., "Outcomes of Rapid Defibrillation by Security Officers After Cardiac Arrest in Casinos", The New England Journal of Medicine, vol. 343(17):1206-1209, Oct. 26, 2000.
Walters et al., "Analog to Digital Conversion Techniques in Implantable Devices", Annual International Conference of the IEEE Engineering in Medicine and Biology Society, vol. 13(4):1674-1676, 1991.
"Installation software for the Right Ventricular Lead Integrity Alert Feature". Medtronic, Inc., Reference Manual M937366A001B: 20, Jun. 17, 2009.
Gunderson et al., "An Algorithm to Predict Implantable Cardioverter-Defibrillator Lead Failure" JACC, vol. 44 (9):1898-1902, Nov. 2004.
All Foreign and NPL References Have Been Previously Provided in Parent Application Serial No. 14203121, Filed on Mar. 10, 2014.
PCT/US2014/022713, International Search Report and Written Opinion, dated Jun. 20, 2014.

\* cited by examiner

METHODS AND DEVICES IMPLEMENTING DUAL CRITERIA FOR ARRHYTHMIA DETECTION

CROSS REFERENCE TO RELATED APPLICATIONS

The present application is a continuation of U.S. application Ser. No. 14/851,138, filed Sep. 11, 2015, now U.S. Pat. No. 9,421,390, which is a continuation of U.S. application Ser. No. 14/203,121, filed Mar. 10, 2014, now U.S. Pat. No. 9,149,645, which claims the benefit of and priority to U.S. Provisional Patent Application No. 61/776,326, filed Mar. 11, 2013, the disclosure of which is incorporated herein by reference.

BACKGROUND

Implantable cardiac stimulus devices, including implantable defibrillators, face competing design goals. A balance must be struck between cautious therapy decisions that avoid inappropriate or unnecessary therapy, and aggressive therapy decisions that prevent syncope and maximize the likelihood of successful revival of the patient. Further alternatives that address these competing goals are sought.

OVERVIEW

The present invention includes implantable devices and methods of operation in implantable devices which implement dual and adaptive arrhythmia detection criteria. The inventors have identified a combination of adaptive and fixed criteria, described herein as a "dual" criteria, for arrhythmia detection. In an example, by observing features of the sensed cardiac signal, one or the other of first and second criteria are selected and applied to the cardiac signal to perform arrhythmia analysis. When indications of highly malignant arrhythmia are identified, first criteria are applied, and when indications of less malignant arrhythmia are identified, second criteria are applied. The criteria that are modified may include persistence or quantity data in one example, such that a greater duration or quantity of evidence is required for apparently less malignant arrhythmias. The invention may be implemented in devices, methods and as non-transitory media containing software instructions.

Further embodiments go beyond "dual" criteria to multiple tiers of criteria and may include the application of a gradient of arrhythmia identification criteria in response to the gradient of potential inputs that exist. In some examples, the electrical cardiac signal is assessed to determine which criteria apply, while in other examples, other inputs are used such as blood constituent levels, blood pressure, accelerometer inputs or communications from other implanted devices.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The following detailed description should be read with reference to the drawings. The drawings, which are not necessarily to scale, depict illustrative embodiments and are not intended to limit the scope of the invention. Unless implicitly required or explicitly stated, the illustrations of methods herein should not be read to require any particular order of steps.

As used herein, a signal is sensed by an implantable cardiac device system, events are detected in the sensed signal, and cardiac rhythms are classified by use of the detected events. Detected events may also be referred to as detections. Classification of the cardiac rhythms may be referred to as rhythm analysis. Cardiac rhythm classification can include identification of malignant conditions, such as ventricular fibrillation or certain tachyarrhythmias, for example.

Implantable therapy systems typically make therapy/stimulus decisions in reliance upon rhythm classification, while monitoring systems typically make data recording decisions using rhythm classification, where applicable. Any of these systems can, if so configured and enabled, generate annunciating (audible tones or palpable vibrations) or communicating (telemetry) signals in response to rhythm classification. The present invention may be used in implantable monitoring or therapy systems.

When detecting events, an implantable cardiac device may compare the sensed signal to a detection threshold. If/when the sensed signal crosses the detection threshold, a new detected event is declared. The detection threshold may be static or may change with time (or by dependence on other variables such as observed signal frequency), depending upon the system configuration. In some systems the detection threshold has a shape defined by a detection profile which can be applied anew after each detected event.

A cardiac cycle typically includes several portions (often referenced as "waves") which, according to well known convention, are labeled with letters including P, Q, R, S, and T, each corresponding to certain physiological events. Each cardiac cycle usually has all of these parts, though not all may be visible on any given cardiac signal representation. Certain components may not be visible due to factors such as elevated rate, choice of sensing vector, anatomic anomaly, or active arrhythmia, for example. The combination of Q, R and S "waves" can be referred to as the QRS complex.

Figure 1:
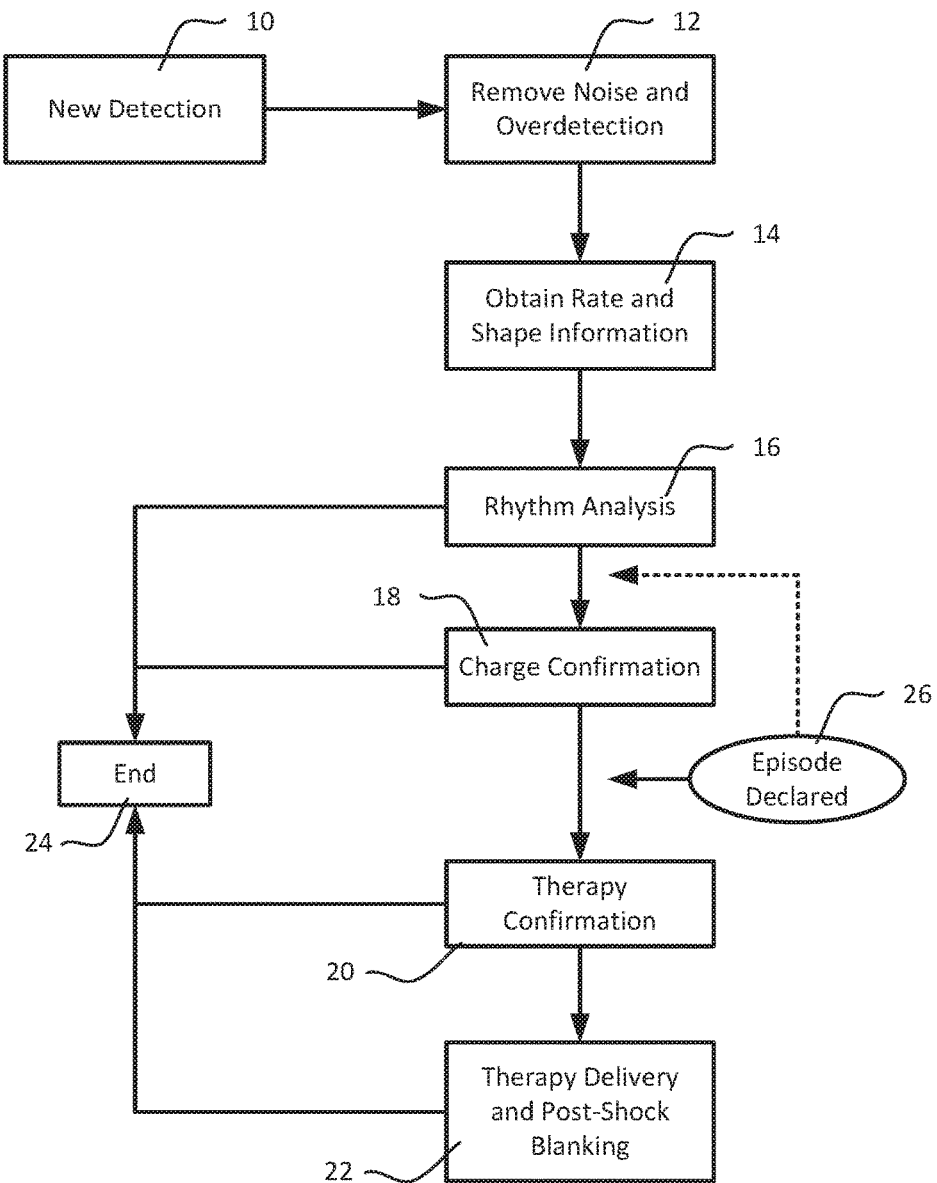
FIG. 1 shows, in block form, a method of analysis in an implantable cardiac device.

The concepts of sensing, detection and rhythm classification are illustratively integrated in the method shown in FIG. 1. An implantable device can be configured to sense signals until a detected event is detected, as previously described. In the method of FIG. 1, a new detection is identified at 10. U.S. Pat. No. 8,565,878, titled ACCURATE CARDIAC EVENT DETECTION IN AN IMPLANTABLE CARDIAC STIMULUS DEVICE, the disclosure of which is incorporated herein by reference, provides several examples of detection profiles and methods/devices for detecting events; other techniques may be used.

The illustrative system next proceeds to removing noise and overdetection as shown at 12. Various methods can be used to identify and remove those detected events caused by noise and overdetection. Some illustrative examples of noise identification are shown in U.S. Published Patent App. No. 2011-0098775, titled ADAPTIVE WAVEFORM APPRAISAL IN AN IMPLANTABLE CARDIAC SYSTEM, the disclosure of which is incorporated herein by reference. Some illustrative examples of overdetection identification are shown in U.S. Pat. No. 8,265,737, titled METHODS AND DEVICES FOR IDENTIFYING OVERDETECTION OF CARDIAC SIGNALS, as well as U.S. Pat. Nos. 8,160,686 and 8,160,687, each titled METHODS AND DEVICES FOR ACCURATELY CLASSIFYING CARDIAC ACTIVITY, the disclosures of which are incorporated herein by reference. Other methods for identifying and removing noise and overdetection may be used instead. It is typical, but not required, to design a detection architecture so that each cardiac cycle is counted once, often by looking for occurrences of the R-wave or QRS complex. In some instances, the P-wave may be observed, instead, as can be the case for a device having an atrial lead.

One approach for block 12 is to identify noisy detections by observing whether a threshold for turning points or inflections, for example, is exceeded. In one example, if at least a threshold number of inflections occur in a period of time associated with a detected event, the detected event is considered suspect due to noise, and suspect events are discarded. In another example, turning points or inflections occurring between detected events may be counted and compared to a threshold, directly or using a per-unit-time metric.

Another approach for block 12 is to identify overdetections by applying criteria to observe patterns of alternating shape of detected events, where alternating shapes may be indicative of overdetection if at least some detections match one another or match a template, while others do not. Another approach for block 12 is to identify overdetection by observing whether a pattern of alternating intervals between detected events appears, where the alternating interval pattern may be indicative of overdetection if the intervals are clustered over time, such as having pairs of long and short intervals. Another approach for block 12 is to identify overdetection by observing whether closely coupled detections have shapes that suggest the two detections are both related to the same QRS complex or beat.

These illustrative methods for noise and overdetection identification may be used in various combinations, and the examples given are merely illustrative. Other techniques may be used.

The removal of noise and overdetection, once identified, can take many forms, including that described in U.S. Pat. No. 8,160,686, which is incorporated herein by reference. For example, detections identified as overdetections may be ignored, allowing the intervals between an identified overdetection and two adjacent-in-time detections to be combined into a single interval for purposes of determining cardiac rate. In contrast, detections identified as suspect, but for which a strong conclusion of overdetection is not available, may be discarded along with the intervals between the suspect event and the two adjacent-in-time detections.

The method also includes obtaining rate and shape information, as shown at 14. Elements of blocks 12 and 14 may overlap or may be performed in different order in various implementations. Rate may be obtained by calculating an average of a number of intervals between detections, where noise and overdetection may be omitted prior to calculating rate. Shape information may include information related to average amplitude, peak amplitude, width, turning points, frequency content and other features as well as sample-by-sample amplitude. Shape information may be generated and/or analyzed by use of correlation waveform analysis, principal component analysis, wavelet decomposition, or Fourier or other mathematical transforms, for example. In some examples, shape information is generated for individual detections. In some examples, shape information is generated for predetermined periods of time that span several detections, for example, calculating data for a 3 second window of time (or other duration).

There are numerous ways of assessing shape information to distinguish malignant from non-malignant cardiac rhythms. Some examples are described in U.S. Pat. No. 7,330,757, titled METHOD FOR DISCRIMINATING BETWEEN VENTRICULAR AND SUPRAVENTRICULAR ARRHYTHMIAS, the disclosure of which is incorporated herein by reference.

In the illustrative example in FIG. 1, the rate and shape information from block 14, along with, if desired, information about results of the assessments of noise and overdetection at 12, are provided to rhythm analysis 16. Rhythm analysis 16, as used herein, includes reviewing a number of detections to classify a patient's cardiac state.

For example, in one illustration, rhythm analysis includes using an X/Y counter by reviewing the analysis of a set of Y detections, and determining how many, X, of the Y detections suggest an ongoing malignant arrhythmia. The calculation of X may include assessment of the rate calculated for at least some of the Y detections, the shape information for at least some of the Y detections, and/or combinations thereof. Some examples in the art use analysis referring to a "number of intervals to detect" marker, sometimes abbreviated as "NID". The NID can be viewed as a subset of X/Y counters in accordance with the approaches illustrated herein.

In an illustrative example, rhythm analysis is tiered. For example, at a first tier, if the rate is above a "VF threshold" when calculated for a given event, that event is considered "treatable" without having to consider other factors. In a next tier, if the rate is below the "VF threshold" and above a "VT threshold" when calculated for a given event, that event is considered "treatable" unless it matches a static template or is both narrow and matches a dynamic template. Finally, in a third tier, if the rate is below the VT threshold when calculated for a given event, that event is not considered "treatable." Other criteria may apply and additional tiers or analytics can be used.

Figure 2:
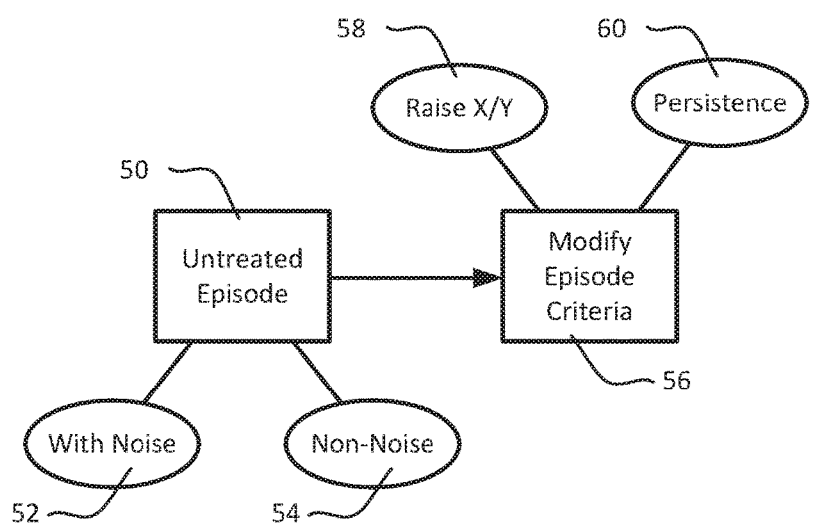
FIG. 2 illustrates, in block form, management of an adaptive arrhythmia detection criteria function.

U.S. Pat. No. 6,754,528, titled APPARATUS AND METHOD OF ARRHYTHMIA DETECTION IN A SUBCUTANEOUS IMPLANTABLE CARDIOVERTER/DEFIBRILLATOR describes certain examples of rhythm analysis, and is incorporated herein by reference. Examples of using an X/Y counter are shown in U.S. Pat. No. 8,160,697, which is incorporated herein by reference. Thresholds such at 8/12, 18/24, 30/40 and higher, as desired, can be used for an X/Y counter, if one is used. For example, if an X/Y threshold of 18/24 is used, if X reaches or exceeds 18, then the X/Y counter condition is met, indicating the likely presence of an arrhythmia. The X/Y counter is not required, though many implantable cardiac systems do incorporate one in their analysis. FIG. 2, below, provides additional discussion of an illustrative method.

Rhythm analysis 16, in the example shown in FIG. 1, can determine that the present rhythm does not appear treatable, in which case the method ends at block 24, until, as indicated by the dashed line leading to block 10, the next new detection occurs. Rhythm analysis 16 may, instead, determine that the present rhythm in fact appears treatable.

If the rhythm analysis 16 concludes that there may be a treatable arrhythmia, the illustrative method continues to a charge confirmation step 18. Charge confirmation 18, in an illustrative example, requires an outcome of rhythm analysis calling for therapy to persist. For example, charge confirmation 18 may require the rhythm analysis outcome to persist for a set period of time, or for a defined quantity of consecutive iterations. In some examples, rhythm analysis 16 and charge confirmation 18 may be combined to a single integrated assessment. In one illustrative example, charge confirmation tracks a variable, "N", and calls for N consecutive iterations of rhythm analysis to reach a result calling for therapy. Some details about modifying persistence are discussed relative to FIG. 2, below.

In the illustration of FIG. 1, an "episode" is declared, as highlighted at 26, following successful completion of charge confirmation 18 finding that therapy should occur. Declaration of an episode can imply several things to those skilled in the art. In some examples, when an episode is declared, certain data, such as an amount of recorded signal data, are stored to longer term memory of the implantable device for later retrieval by a physician. Episode declaration may also coincide with the beginning of preparations for therapy delivery, such as charging of a capacitor to enable therapy delivery.

In some examples, an episode declaration coincides with the device entering a "concerned" state, causing heightened analysis to initiate and data storage, but without preparation for therapy beginning. For example, an episode may be declared before charge confirmation 18, as indicated by the dashed line from episode declaration 26 shown in FIG. 1.

Episode declaration may lead to or coincide with the start of delivery of anti-tachycardia pacing (ATP). Episode declaration may coincide with annunciation of a warning signal to a patient or healthcare system, such as by generating an audible tone or vibration to alert the patient of potential impending therapy delivery or generation of an electronic transmission, such as by RF or other telemetry, to a monitoring or programming system, or generation of an emergency alert for transmission to emergency services.

In the illustrative method, the next block of decision making is at therapy confirmation 20. Therapy confirmation 20 takes place, in this example, once preparations for therapy are complete or nearly complete. For example, a capacitor for high voltage therapy delivery may be charged or nearly completed with charging. In some examples (where ATP is included), ATP delivery may be completed but the episode fails to terminate in response to ATP. For such an example, the ATP may be delivered once block 18 is passed, but high energy shock for defibrillation will wait until the ATP is complete and therapy confirmation 20 is satisfied.

For example, therapy confirmation 20 can include checking that select criteria indicating a malignant arrhythmia continue to exist. In one illustrative example, therapy confirmation 20 checks that the detected rate of cardiac events for the patient exceeds a therapy limit immediately before therapy delivery. Some illustrative examples of therapy confirmation are shown in U.S. Published Patent App. No. 2010-0331904, titled ADAPTIVE CONFIRMATION OF TREATABLE ARRHYTHMIA IN IMPLANTABLE CARDIAC STIMULUS DEVICES, the disclosure of which is incorporated herein by reference. Other checks may be performed in therapy confirmation 20, or, alternatively, therapy confirmation 20 may be omitted.

Upon completion of therapy preparations and passing of each of the analytical blocks 16, 18 and 20, therapy can be delivered at block 22. Therapy delivery can be performed in any suitable fashion, including transvenous, epicardial or subcutaneous electrodes in various combinations and energy levels. Various commercially available systems that can deliver therapy are known including the Boston Scientific Teligen® ICD and S-ICDO System, Medtronic Concerto® and Virtuoso® systems, and St. Jude Medical Promote® RF and Current® RF systems. Some examples of subcutaneous-only therapy delivery are shown in U.S. Pat. No. 8,244,349, titled ADAPTIVE SHOCK DELIVERY IN AN IMPLANTABLE CARDIAC STIMULUS DEVICE, the disclosure of which is incorporated by reference.

Following therapy delivery, there may be some period of post-shock blanking and various other activities may occur as indicated at 22. In one illustrative example, the methods of U.S. Pat. No. 8,494,630, titled DATA MANIPULATION FOLLOWING DELIVERY OF A CARDIAC STIMULUS IN AN IMPLANTABLE CARDIAC STIMULUS DEVICE, the disclosure of which is incorporated herein by reference, are applied to prepare the implantable device, following therapy delivery, for further analysis. Multiple shocks may be delivered during a particular episode. In some examples, one or more analysis steps in FIG. 1 may be modified following delivery of a first therapy shock during a given episode.

Certain steps shown in FIG. 1 may be simplified or omitted in some embodiments. In illustrative examples, additional elements are used to adjust the processes followed in one or more of blocks 16, 18 or 20 to render the overall therapy decision more aggressive or less aggressive in response to identified criteria. Additional steps/processes beyond those shown may be performed in some embodiments. For example, anti-tachycardia pacing may be applied before or after charge confirmation 18 and/or episode declaration 26.

FIG. 2 illustrates, in block form, management of an adaptive arrhythmia detection criteria function. The method starts with the identification of a nonsustained episode at block 50. A nonsustained episode is one in which therapy is not delivered following episode declaration.

One example of a nonsustained episode is an episode that is caused by intermittent noise or by noise that terminates before therapy delivery, such as intermittent/temporary skeletal noise or external noise. Such noise may cause the implantable device to mistakenly identify a high rate cardiac arrhythmia; where noise is intermittent and ceases before delivery of therapy, modern devices generally will not deliver a shock if the end of high rate conditions is identified before therapy delivery. Another source of such episodes can be lead failure or impending lead failure, a known source of both nonsustained and treated noise-related episodes in transvenous ICD patients. These would be nonsustained episodes with noise, as indicated at 52.

A nonsustained episode can also occur, for example, if the patient has a nonsustained ventricular tachycardia, meaning that short burst of high rate detected events has occurred.

Another example is an episode that begins due to malsensing of the cardiac signal (such as double detection) which subsequently resumes accurate detection. Such episodes would be non-noise untreated episodes 54.

In response to the nonsustained episode, the detection architecture can be configured to modify the episode criteria, as indicated at 56. Some examples include raising the parameters used to define arrhythmia in an X-out-of-Y counter by modifying X and/or Y.

One particular example of modifying episode criteria is to raise the criteria applied for an X/Y counter, as shown at 58. Another example of modifying episode criteria is the extension of persistence criteria 60. Illustrative discussions for each of raising X/Y counter criteria 58 and applying persistence criteria 60 are provided in U.S. Pat. No. 8,160,697, which is incorporated herein by reference. Such modifications, in part, should reduce the sensitivity to nonsustained episodes and can delay episode declaration for a particular system to avoid repeated declarations of episodes, which may unnecessarily use up battery capacity and/or increase the likelihood of inappropriate therapy delivery. However, such changes may also delay the declaration of an episode for those events which do require therapy, such as sustained ventricular fibrillation.

Figure 3:
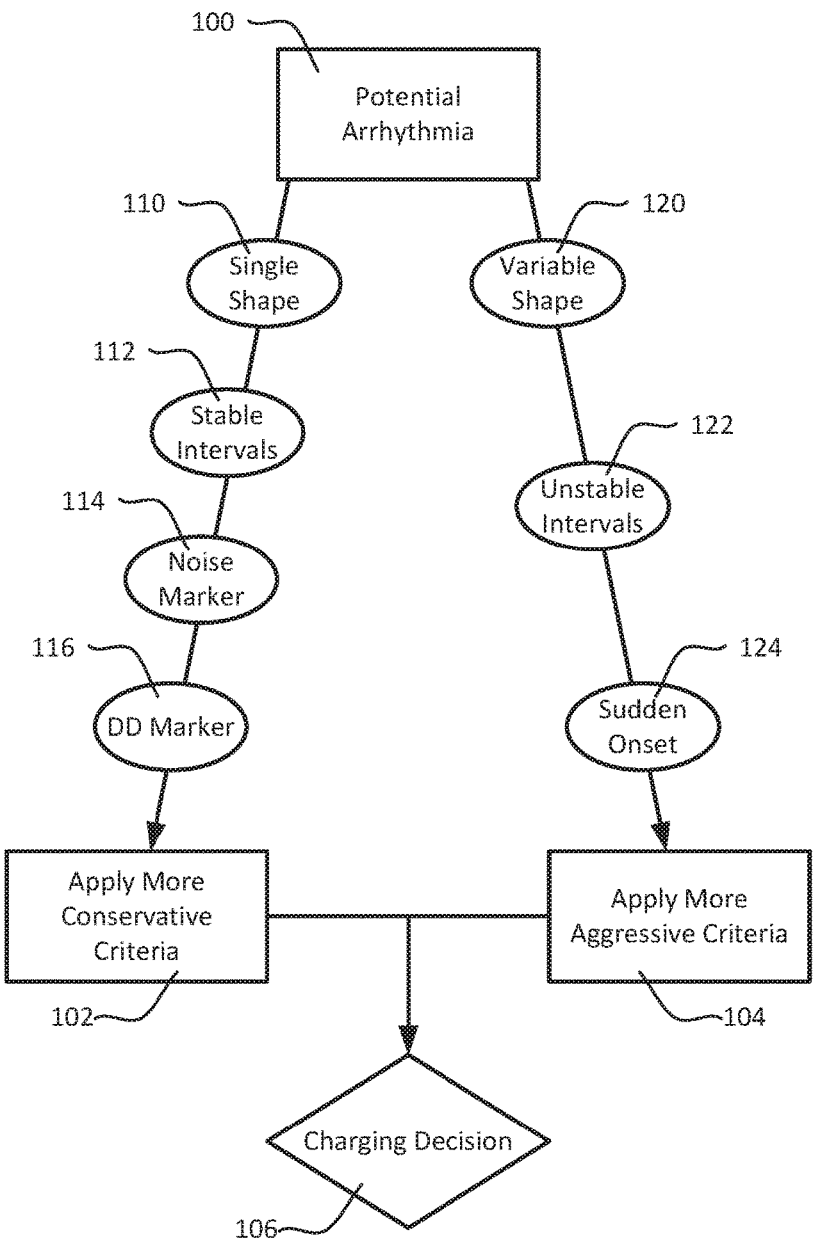
FIG. 3 shows in a block/flow format, the selection between first and second criteria for arrhythmia identification.

FIG. 3 shows in a block/flow format, the selection between first and second criteria for arrhythmia identification. The method illustrated in FIG. 3 is intended to address and prevent delays due to selection of less sensitive and more conservative criteria to arrhythmia identification and, when certain signal characteristics are noted, to switch to more aggressive criteria for arrhythmia identification.

In the illustrative example, analysis begins with the identification of a potential arrhythmia at 100. Once a potential arrhythmia is identified at 100, the method determines which, if any, of various features are found in the ongoing cardiac condition. Using such features, either more conservative criteria 102 or more aggressive criteria 104 is applied to make the charging decision 106.

In one example, a potential arrhythmia triggering the analysis is any rate above a predetermined threshold. For example, a (cardiac) rate of 150 beats-per-minute (bpm) may be a threshold to begin assessing which arrhythmia identification criteria 102 or 104 to apply. Other rates may be chosen, for example, in the range of 100 to 250 bpm. A potential arrhythmia could also be identified through shape (morphology) analysis, through assessment of cardiac signals captured in a block of time, by frequency transform/analysis, or other methods. In another example, if an X/Y counter is to be applied, the decision process of FIG. 3 may be applied as soon as the most aggressive arrhythmia detection criteria is met; in one such embodiment, an X/Y at 12/16 is applied in the "aggressive criteria"104, while X/Y at 18/24 is applied in the "conservative criteria", and the method of FIG. 3 is performed once either of 18/24 or 12/16 is met.

In another approach to the "potential arrhythmia" 100, the system may track counts of "accelerators" and "inhibitors" and, upon the count of "accelerators" exceeding a threshold, block 100 would be satisfied. The individual blocks on each arm in FIG. 3 can be used for this purpose. For example, any of blocks 110, 112, 114 and 116 could be described as "inhibitors", while blocks 120, 122 and 124 would be described at "accelerators". The analysis of accelerators and inhibitors would occur on a beat to beat basis, thus, if, when looking at two beats back to back, the interval between the beats is significantly different from a preceding interval, that could be counted as an unstable interval 122 and/or sudden onset 124 accelerator. When the number of accelerator counts exceeds the number of inhibitor counts—directly or by some quantity or margin, for example—block 100 would be met.

The option to select between block 102 and block 104 provides the system with dual criteria for arrhythmia identification. In some examples, at least one of the dual criteria can also be adaptive, for example as shown below in FIG. 6.

Features of the cardiac signal that are identified in the illustrative example of FIG. 3 as indicating the application of more conservative criteria 102 include identification of a "single shape" 110, meaning that the cardiac signal is repeating and consistent in morphology. Examples of identifying a "single shape" 110 signal may include assessment of whether the shape of the QRS complex, R-wave, T-wave, or other feature, of a given detected event is compared to the shape of the same feature for a preceding detected event.

Additional features that can be checked in "single shape" 110 analysis include amplitude and width, singly or in combination. If the shape of the feature chosen is generally the same from one detected event to the next, then the cardiac signal has a "single shape." Alternatively, the shape may be compared to several preceding events or to an average shape. This may also be described as a monomorphic cardiac signal. In some alternative embodiments, a transform may be used, for example, a Fourier, Laplace, Principal Components Analysis or wavelet transform may be used, or the shape may be determined for the first or second derivative and that shape may be compared from one detected event to the next.

Another feature noted favoring the application of more conservative criteria is interval stability 112. For example, the interval from one detected event to the next may be compared to a preceding interval; if the intervals are similar (within predefined boundaries, for example), then stable intervals 112 are found.

Additional features noted favoring the application of more conservative criteria include the existence of noise markers 114 and double detection markers 116. For example, if a threshold number of noise markers 114 or double detection ("DD") markers 116 are observed in a given block of time or given quantity of detected events, then the illustrative method applies the more conservative criteria. Multiple tiers or criteria may apply in this illustrative example, for example, if a noise marker is identified in the previous 8 detected events, or three noise markers in the previous 24 detected events, then the illustrative example would apply the "more conservative" criteria 102. In another example, if there are three DD markers in the previous 20 seconds of data, then the more conservative criteria 102 may apply. There may be several numerical approaches to the application of rules for noise markers 114 and DD markers 116.

In the illustrative example of FIG. 3, two of the features that favor application of more aggressive criteria include variable shape 120 and unstable intervals 122. These features may be found when assessment 110 and 112, respectively, fail. Another feature that favors application of more aggressive criteria is that of sudden onset 124. A sudden onset may be identified if the observed rate of detected events rises quickly, for example, if the average rate increases from under 100 bpm to over 180 bpm in less than one second and remains elevated. In an illustrative "sudden onset" assessment, a percent of change criteria from one R-R interval to the next may be applied. Other criteria may apply.

There are several combinations that may apply to reach one criteria result or the other 102, 104. All or selected subsets of the noted features 110, 112, 114, 116, 120, 122, 124 may be contemplated. Some illustrative examples include:

In a first example, if the cardiac signal is variable in shape (120=true and 110=false) and no noise markers or DD markers (114=false and 116=false) have occurred in the most recent 8 events, more aggressive criteria 104 apply.

In a second example, if any two of variable shape 120, unstable intervals 122, or sudden onset 124 occur, then the more aggressive criteria 104 apply, else, the more conservative criteria 102 apply In a third example, any one of variable shape 120, unstable intervals 122 or sudden onset 124 will cause the more aggressive criteria to apply except if noise markers 114 or DD markers 116 have been observed.

In a fourth example, either variable shape 120 or unstable intervals 122 will cause the more aggressive criteria to apply unless DD Markers 116 have been observed (though noise markers 114 do not negate variable shape 120 or unstable intervals 122 in this example), and sudden onset 124 will also cause the more aggressive criteria to apply unless noise markers 114 have been observed (though DD Markers would not negate sudden onset 124 in this example). It should be noted that rate is not one of the features that drive selection of the more conservative or more aggressive criteria. Thus the illustrative approach is different from tiered analysis zones known in the art, where VT and VF rate zones are defined so the VT zone covers lower rates than the VF zone and entails morphology analysis of detected events, while VF rate zone covers the highest rates is a purely rate-based determination. U.S. Pat. No. 6,754,528, titled APPARATUS AND METHOD OF ARRHYTHMIA DETECTION IN A SUBCUTANEOUS IMPLANTABLE CARDIOVERTER/DEFIBRILLATOR, the disclosure of which is incorporated herein by reference, describes examples of tiered zone analysis. In addition, by omitting rate from the consideration of which of conservative or aggressive criteria is selected, the present invention differs from examples which apply separate NID or X/Y criteria to VF and VT zones, for example.

In an illustrative example, the "More Conservative" criteria applied at 102 will be different from the "More Aggressive" criteria applied at 104. For example:

More Conservative criteria applies an X/Y Counter set at 18/24 with persistence set to 3; More Aggressive criteria applies an X/Y counter set at 12/16 with persistence set to 2

More Conservative criteria applies an X/Y Counter set to 30/40; More Aggressive criteria applies an X/Y counter set at 18/24 with no persistence by default in either criteria More Conservative criteria applies an X/Y Counter set at 18/24 with variable persistence at a minimum of 2 and extends if nonsustained episodes occur; more Aggressive Criteria applies an X/Y Counter set at 18/24 with fixed persistence set to 2. In this example, the X/Y Counter at 18/24 and persistence may be referred to as a default value. In this last configuration, FIG. 3 would become effective to undo, under selected circumstances, the extensions of X/Y criteria and or persistence criteria created in the illustrative example shown in FIG. 2.

In another example, as shown below in FIG. 8, the combination of multiple criteria can be used to select from conservative, aggressive, or dynamic criteria. In some embodiments, a range of conservative to aggressive criteria may be available to allow selection of the criteria to apply to be made in proportion to cardiac signal characteristics.

In one example, block 100 may correspond to the delivery of anti-tachycardia pacing therapy. During the delivery of such therapy, ongoing analysis takes place to determine whether the system ought to proceed to more aggressive therapy regimen(s). The review of the differing criteria of the detected rhythms can take place as a device moves through a progression of therapy decisions. Moreover, as the criteria are applied, delivery of an existing therapy (such as ATP) may be terminated if a sufficient number of factors favoring a conservative approach (such as factors 110, 112, 114, 116) are identified.

Figure 4:
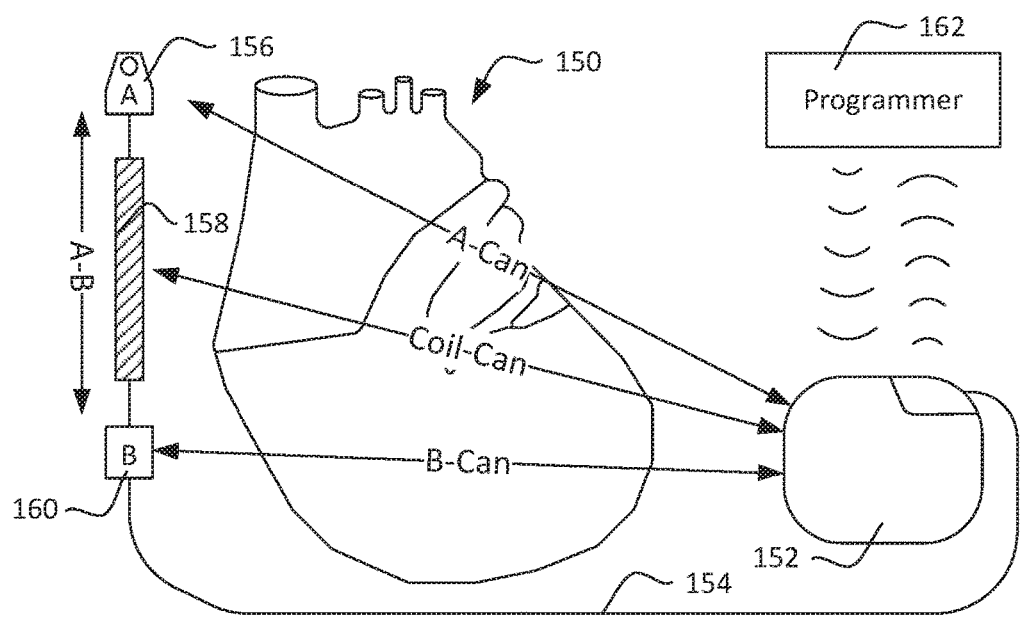
FIGS. 4-5 illustrate subcutaneous-only and transvenous implantable cardiac stimulus devices.
Figure 5:
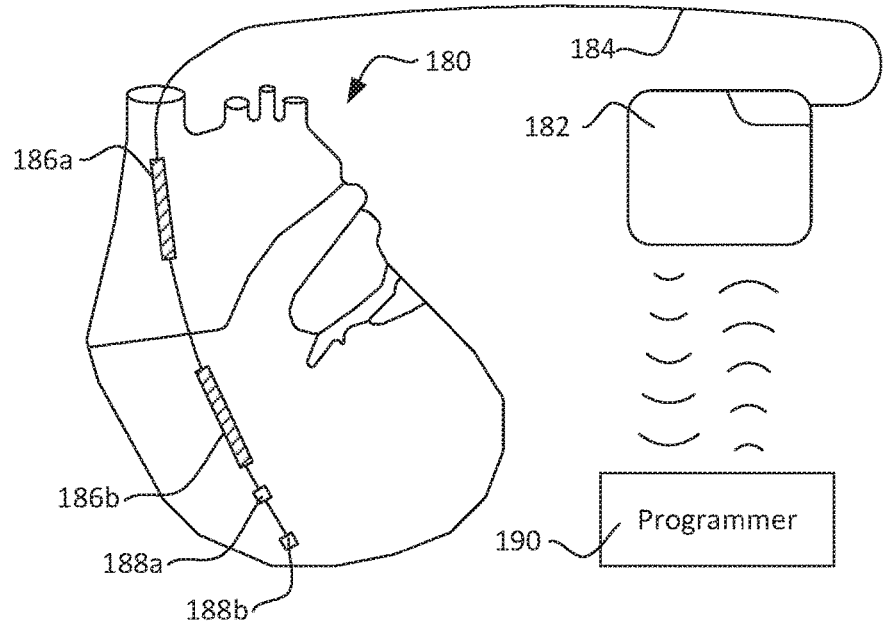

FIGS. 4-5 illustrate subcutaneous-only and transvenous implantable cardiac stimulus devices. Any implantable cardiac device may use the methods illustrated herein, including the subcutaneous-only implantation shown in FIG. 4, and the transvenous implantation shown in FIG. 5. Epicardial and/or entirely intravascular or intracardiac implantation may be used instead.

Referring now to FIG. 4, the system is implanted in a patient (whose anatomy other than the heart 150 is largely not shown), with a canister 152 placed near the left axilla at about the level of the inframammary crease. A lead 154 extends medially toward the xiphoid and then extends along the side of the sternum toward the head of the patient. It can be seen that the subcutaneous implantation occurs at locations exclusive of the heart 150, and does not contact or enter the heart 150, avoiding the various known risks associated with entering or touching the heart.

The lead 154 is shown with a plurality of electrodes 156, 158, 160, though more or fewer electrodes can be provided. Electrode 160, nearest the xiphoid, is shown as a ring electrode, middle electrode 158 is shown as a coil electrode, and tip electrode 158 is shown as having an attachment hole; these features and electrode designs may be interchanged, modified, or replaced with any suitable electrode design known in the art. Some illustrative designs are shown in U.S. Pat. No. 8,483,841, titled ELECTRODE SPACING IN A SUBCUTANEOUS IMPLANTABLE CARDIAC STIMULUS DEVICE, and U.S. Published Patent App. No. 2012-0029335, titled SUBCUTANEOUS LEADS AND METHODS OF IMPLANT AND EXPLANT, each of which is incorporated herein by reference. Additional examples which may also function are shown in numerous other patents and patent applications and/or are or once were commercially available as implantable electrodes of various types.

The canister 152 may include an electrode formed as a discrete electrode, as a portion of the surface of the canister 152, or as entire surface of the canister 152. The canister 152 preferably contains operational circuitry for the system. The operational circuitry may include a controller and any suitable analog and/or digital circuits needed for signal processing, memory storage and generation of high-power, low-power electrical or non-electrical outputs. The operational circuitry may be coupled to suitable battery technology for an implantable device, with any of numerous examples well known in the art, and may use various capacitor technologies to assist in the short term build-up and/or storage of energy for defibrillation or other high output purposes.

In one example, operational circuitry includes a set of input switches or a multiplexor associated with analog filtering circuitry such as DC filtering capacitors coupled to an input amplifier. The input amplifier may be associated with additional filtering, such as a bandpass filter, if desired. If multiple sensing vectors are assessed, there may be more than one input amplifier circuit. The output of the input amplifier(s) may couple to the inputs of analog-to-digital conversion (ADC) circuitry, which provides one or more digital signal outputs to a processor or controller. Digital filtering may be performed in the ADC circuitry and/or the associated processor or controller.

Memory, including, for example, RAM and/or flash memory, or other media, is accessible by the processor/controller for obtaining instructions for operation as well as storing episodes, performance data, signal data, parametric settings, device information, etc. The operational circuitry can include or be coupled to one or more batteries to power the implantable system as well as output circuitry and, in higher powered implementation, capacitor and charging circuits for producing defibrillation outputs from the battery power. As noted above, there are a number of commercially available implementations of devices having suitable operational circuitry for performing the methods herein and/or for being configured to perform such methods.

The lead 154 and external shell for the canister 152 can be manufactured with various materials suitable for implantation, such as those widely known, along with coatings for such materials, throughout the art, as well as materials used with the commercial devices noted above. For example, the canister can be made using titanium, with a titanium nitride or iridium oxide (or other material) coating if desired, and the lead can be formed with a polymeric material such as a polyether, polyester, polyamide, polyurethane or polycarbonate, or other material such as silicon rubber. The electrodes 156, 158, and 160 can be formed of suitable materials as well, such as silver, gold, titanium or stainless steel such as MP35N alloy, or other materials. Systems may have features allowing use in magnetic resonance imaging systems.

The location of system implant may vary. For example, the system shown in FIG. 4 is a subcutaneous-only system located on the anterior and lateral chest between the skin and ribcage of the patient. Other subcutaneous only systems (including systems without a lead 154, with multiple leads 154, or an array in place of lead 154) may be used with other anterior only placements and/or anterior-posterior, posterior only, left-right, etc. locations, including, for example, locations and designs noted in U.S. Pat. No. 6,647,292, U.S. Pat. No. 6,721,597, U.S. Pat. No. 7,149,575, and U.S. Pat. No. 7,194,302, each of which is incorporated herein by reference, and other locations as well. Subcutaneous placement can include any location between the skin and ribcage, including sub-muscular.

A programmer 162 is shown as well. The programmer 162 and implantable system are preferably designed to communicate with one another during programming sessions. Such communication may include interrogation of device history and/or status, reprogramming of device settings, updating or downloading of new software/firmware, control of testing of the system such as induction or pacing testing, lead impedance or battery measurement, etc. While a programmer 162 is shown, it is understood that any suitable monitoring system (such as a home monitoring system) can take the place of the programmer 162 for any of these noted functions, as desired. As noted, there are various vectors for sensing and/or therapy delivery defined by the electrodes 156, 158 and 160 and can 152.

FIG. 5 illustrates a transvenous implantation. In this example, the system is implanted in the patient, whose anatomy other than heart 180 is not shown. An implantable canister 182 is illustrated and may be generally similar to canister 152 described above in terms of physical features and contents (though certain energy outputs and signal sensitivities may be configured for transvenous rather than subcutaneous use).

Lead 184 is coupled to the canister 182, and enters the subclavian vein and passes through the vasculature into the heart 180. The lead 184 includes coil electrodes 186a and 186b, as well as ring electrodes 188a and 188b. Other avenues of access to the heart 180 may be used instead.

An external programmer 190 may be used to communicate with the implanted device 182 for various reasons. A number of vectors for sensing and/or therapy are defined by the electrodes 186a/b, 188a/b and canister 182. Other implant locations and approaches can be used instead, and additional or fewer electrodes and leads may be used. There are numerous commercially available implantable cardiac stimulus and/or monitoring systems having similar and different designs in which examples of the present invention may be implemented by those skilled in the art. Some examples may include dual chamber devices, single chamber devices, biventricular devices, atrial-only devices, etc. Systems with quadripolar or other multipolar leads designed to allow flexible selection of sensing and stimulus electrodes may be used as well.

Several illustrative examples take the form of implantable cardiac stimulus devices such as implantable cardioverter-defibrillators, implantable pacemakers, and/or hybrid/combinations that include each of implantable defibrillator capabilities and implantable pacemaker capabilities, including cardiac resynchronization therapy devices. Other illustrative examples may include implantable cardiac monitors, which can use arrhythmia classification methods to determine when and how to perform such functions as generating patient alerts, identifying captured signal data for storage, or any other suitable functions. Some examples may also include the ability to deliver pharmaceuticals, nerve stimulation/modulation, or any other suitable therapy. Such systems can be combined with other implantable devices for similar or different purposes and may be configured to communicate with other implantable devices using various known approaches such as RF communication or communications encoded in stimulus or sub-stimulus outputs.

Figure 6:
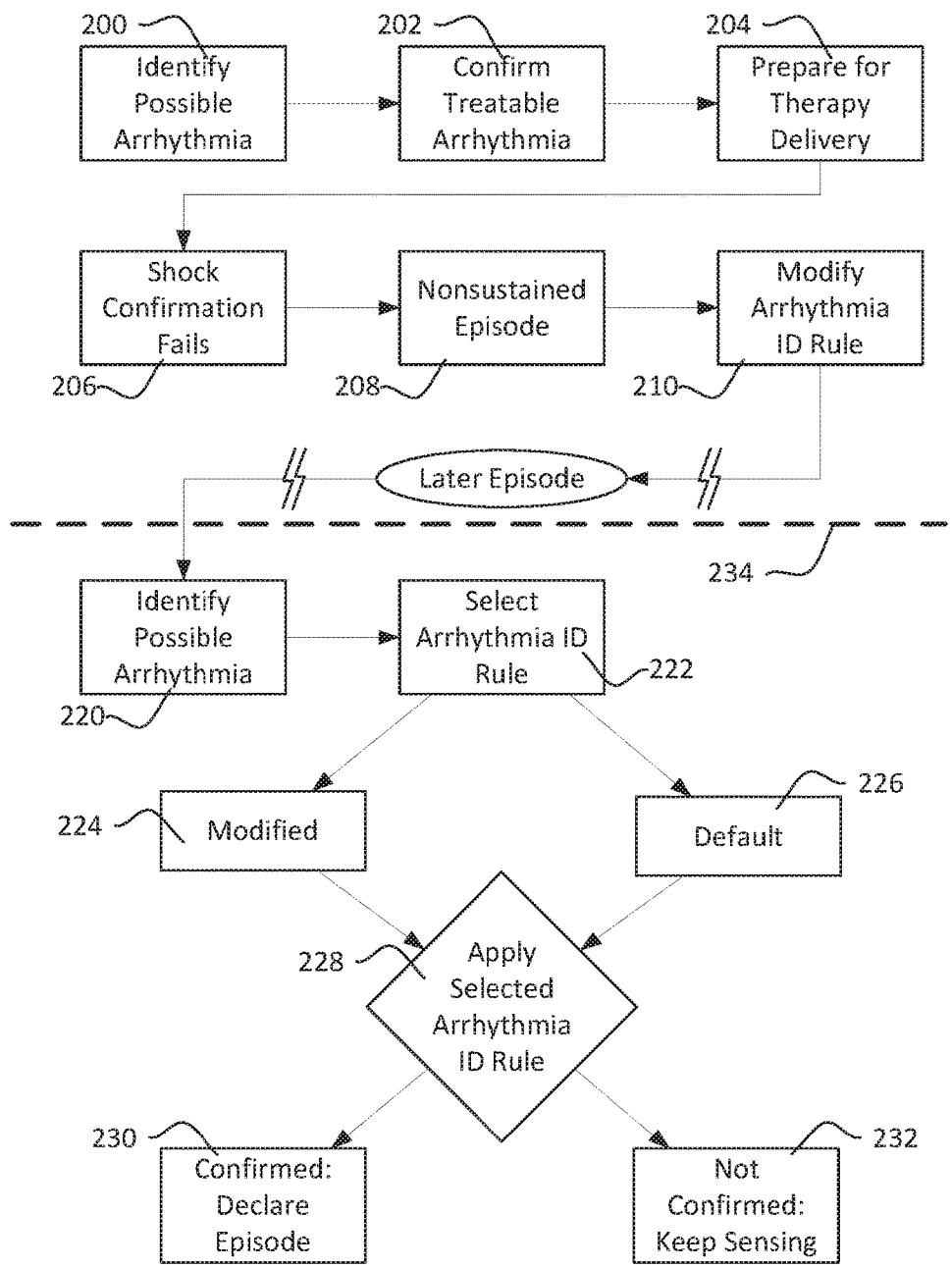
FIG. 6 shows, in block form, a method of analysis.

FIG. 6 shows, in block form, another method of analysis. The illustrative method begins at block 200 with the identification of a possible arrhythmia, methods for which are noted above. Next, the method includes confirming that a treatable arrhythmia 202 is occurring through the use of arrhythmia identification parameters or rules, prompting the initiation of therapy preparations 204, which may include starting a charging operation for a capacitor(s) for delivery of defibrillation stimulus. In this example, however, shock confirmation later fails as shown at 206, meaning that the identified treatable arrhythmia ceased to be detected before therapy can be delivered. For example, the patient's cardiac rate may have dropped below a treatable zone. As a result, a nonsustained episode 208 is identified as having occurred. In accordance with the illustrative method, one or more attributes of the arrhythmia identification parameters or rules are modified at 210 in response to the identification of a nonsustained episode. These modified parameters are stored for use in a later episode.

The later episode begins again with identification of a possible arrhythmia at 220, which is followed by selection of the Arrhythmia Identification Rule at 222. This selection step 222 can be performed as illustrated above in FIG. 3. If conditions of the cardiac rhythm suggest the use of the more conservative, modified criteria 224, here, a rule as modified at block 210, then the modified criteria 224 are selected at 222 for use in the decision step at 228, which applies the selected Arrhythmia Identification Rule. Alternatively, if the conditions of the cardiac rhythm suggest the use of a more aggressive rule, in this instance, the default rule applied without modification by block 210, the default Arrhythmia Detection Rule 226 is then applied in the decision at block 228.

From the decision block, either the arrhythmia is confirmed and an episode is declared at 230, or the arrhythmia is not confirmed and the system continues sensing as shown at 232. Once the episode is declared at 230, steps for preparation of therapy delivery and eventual shock confirmation can be performed, similar to blocks 204 and 206. If another nonsustained episode occurs, the modification of the arrhythmia identification rule at 210 may be repeated, within whatever limits to extensions, X/Y counter and persistence rules may be selected for a given system.

In this illustrative example, the availability of dual criteria 224, 226 may allow quicker identification of an arrhythmia in certain circumstances, while retaining the potential benefit of applying more conservative criteria in other circumstances. This option also allows the modified criteria 224 to become adaptive to the patient by use of the modification at 210.

In another example, the existence of a previous episode can be left out of the method, with the blocks above line 234 omitted. In this example, the arrhythmia identification rule is automatically selected at 222 whenever a possible arrhythmia 220 has been identified. In yet another example, following delivery of therapy in a given episode, a re-selection of the arrhythmia identification rule may take place by observing characteristics of the then occurring detected signal.

While the example of FIG. 6 presumes that episode declaration coincides with or immediately leads to preparing for therapy delivery, in other examples, there may be additional steps between blocks 202 and 204. For such an example, episode declaration would cause a first set of activities (such as annunciation of the episode, data storage, ATP) to begin, with preparation for high power therapy delivery (i.e. defibrillation or cardioversion) following later if the arrhythmia continues.

Figure 7:
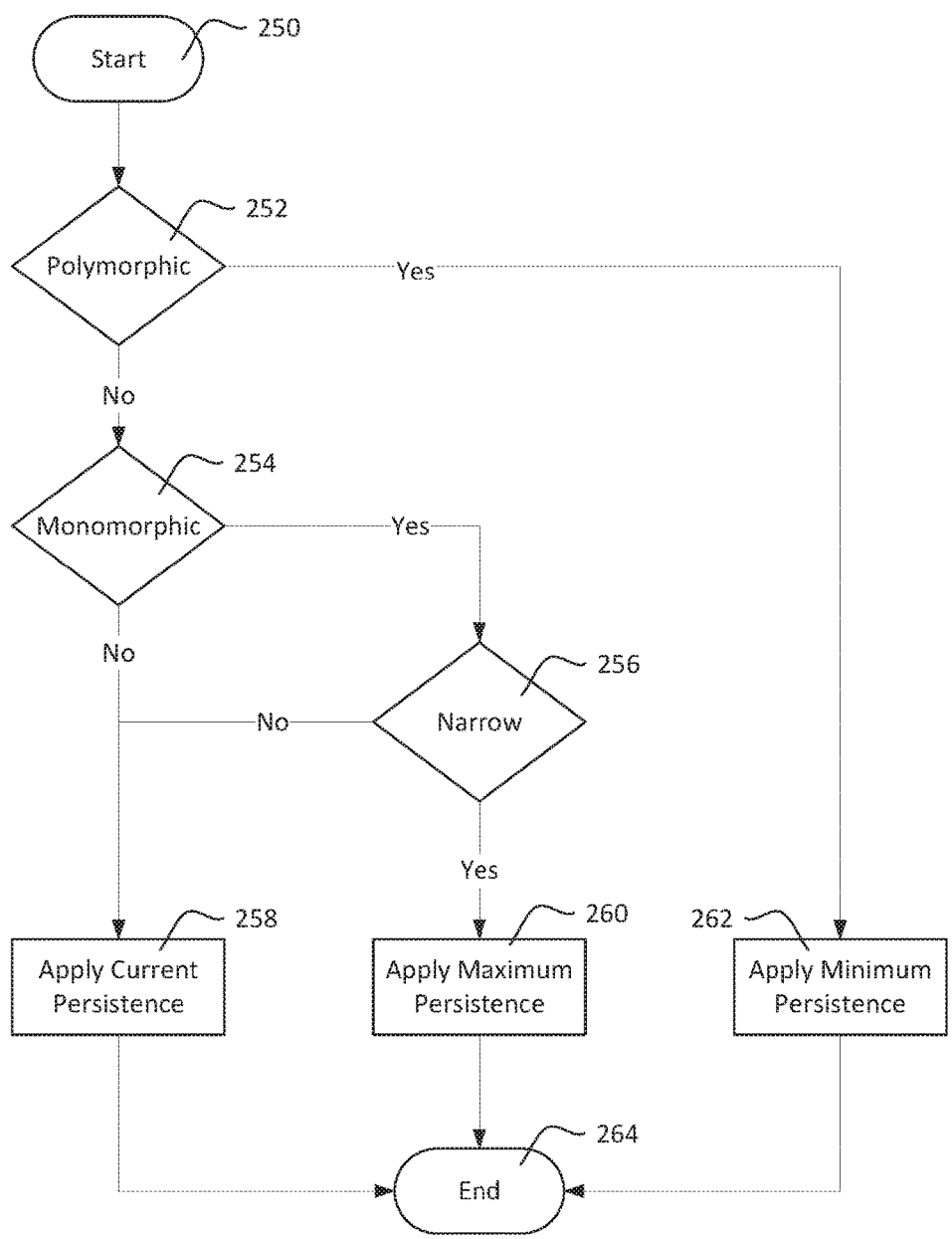
FIG. 7 shows another illustrative embodiment in block form.

FIG. 7 shows another illustrative embodiment in block form. In this embodiment, a method of selecting arrhythmia identification parameters is illustrated, and three outcomes are possible, as will be shown. Beginning from start block 250, the method is presumed to already have made a preliminary showing of some potential arrhythmia, for example, by determining that an elevated beat rate has been identified. This preliminary showing may be omitted from some embodiments.

From block 250, the method determines whether the observed cardiac signal is polymorphic, noted at 252. For example, correlations (using, for example, correlation waveform analysis, difference of area analysis, principal components analysis, wavelet analysis or other features) for a number of detected events to a static or dynamic template may be observed. If the outcomes of such correlations vary widely, then the shape of the signal is considered polymorphic. Polymorphic rhythms are of higher concern in this embodiment, and so if the cardiac signal is found to be polymorphic, the minimum amount of persistence is applied, as shown at 262, with the method of selecting arrhythmia identification parameters then ending. The method may be repeated for each individual detected event, or a determination may be made for a set of events, periodically at set intervals, or as desired. One effect of modifying the arrhythmia criteria to use minimum persistence (or other criteria) in response to the identification of polymorphic arrhythmia may be to reduce the time to therapy. Since polymorphic arrhythmias typically require quick therapy, this may yield patient benefits.

If the cardiac signal is not polymorphic at 252, the method next determines whether the cardiac signal is monomorphic, as shown at 254. In the example of FIG. 7, separate definitions for monomorphic and polymorphic are defined. For example, block 252 may look for a string of correlations to a static template that vary from one to the next, while block 254 may look at an individual detected event comparison to a dynamic template that updates from beat to beat. If the signal is not monomorphic at 254, then the current persistence 258 is applied. By current persistence 258, the method is referring to the persistence requirements that the system has defined by use of its own experience. For example, if the default persistence has been extended once in response to a prior nonsustained episode, then the extension will continue to apply using the "current" persistence.

If the cardiac signal is monomorphic at block 254, using the definitions in the example, the method next determines whether the signal is narrow, as shown at 256. If the signal is not narrow, the method will apply the current persistence at 258. On the other hand, if the signal is both monomorphic 254 and narrow 256, the method will apply a maximum persistence value(s) before determining that therapy is needed as shown at 260. In this example, the monomorphic and narrow aspects of the detected rhythm suggest that the rhythm may not be as dangerous as polymorphic or wide arrhythmias.

For example, some monomorphic ventricular tachycardias are well tolerated by patients, particularly if narrow events are observed. Such features may indicate an exercise induced ventricular tachycardia, which generally would not need therapy. Typically the physician will select VT zone rates to accommodate exercise induced "normal" high rate conditions, however, brief excursions of the cardiac rate above the defined zone may occur depending on patient conditions.

In one example relating to FIG. 7, an episode may be declared prior to selecting the arrhythmia classification parameters. In this example, start block 250 corresponds to episode declaration, leading to data storage at least for the event. Whether a therapy is ever called for may rely on the application of the selected criteria from FIG. 7.

One distinction between FIG. 7 and FIG. 6 is that, in FIG. 6, the decision of which of the different arrhythmia criteria to apply is shown as occurring after at least one nonsustained episode has been identified. In FIG. 7 (and FIG. 8 as well), there is no need for a prior nonsustained episode to have taken place. Instead, the device simply uses the cardiac signals as detected to select from among multiple arrhythmia detection criteria it may apply.

The illustration in FIG. 7 uses monomorphic and polymorphic morphology assessments at 252, 254, and joins the analysis of whether detected event(s) are narrow at 256. Other features may be used, including, for example, those discussed in U.S. Pat. No. 7,330,757, the disclosure of which is incorporated herein by reference. For example, correlation to a template—any template—may suggest a non-polymorphic signal for which more conservative parameters may be applied. High variability of correlation scores, from one event to the next, regardless what template (whether dynamically updating or statically stored) may suggest a more aggressive approach to a therapy decision. Rate accelerating events and low interval stability are both suggestive of more aggressive approaches to therapy decisions.

Figure 8:
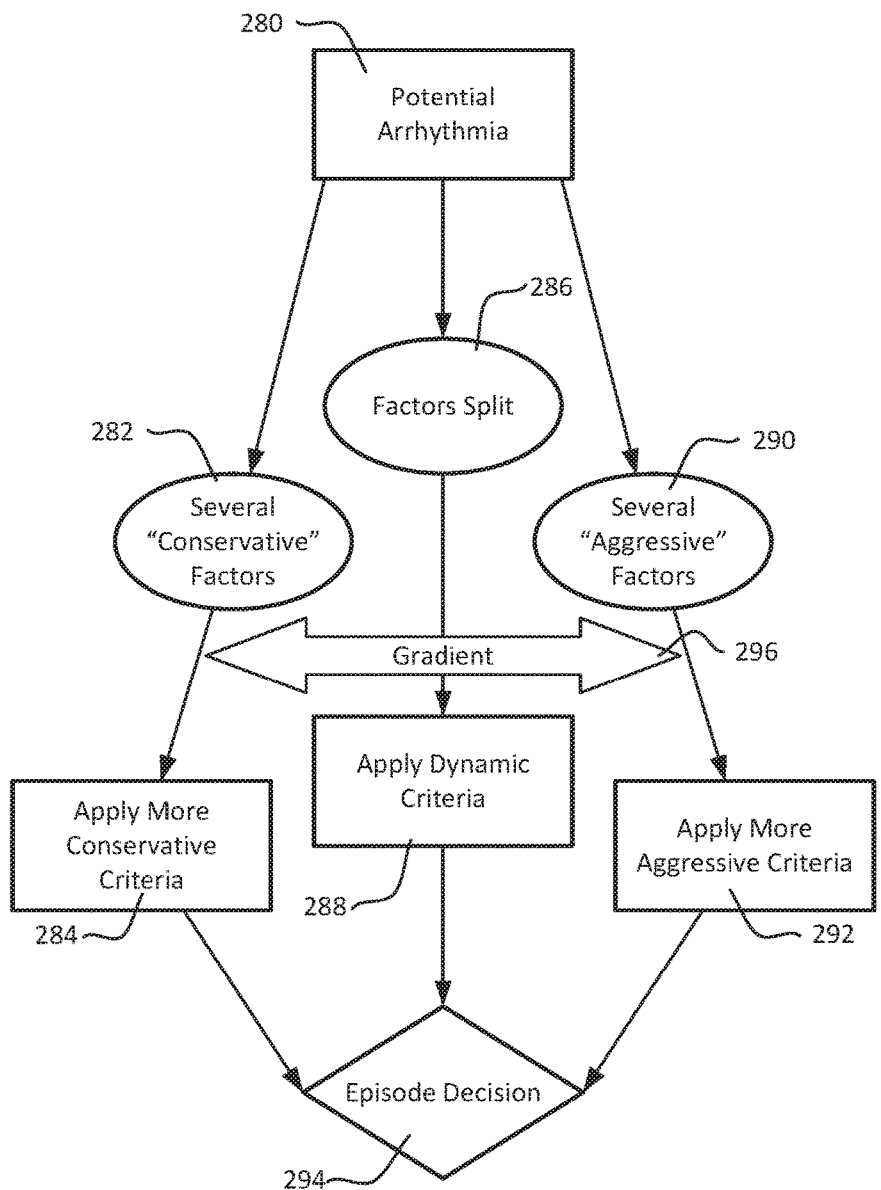
FIG. 8 illustrates another method of analysis.

FIG. 8 illustrates another method of analysis. In this method, a potential arrhythmia is identified at 280. Upon identification of a potential arrhythmia, an assessment of factors that support use of aggressive or conservative arrhythmia analysis occurs. Illustrative factors include beat-to-beat amplitude, width or spectral content similarity, with similarity of one or more of these factors supporting use of conservative analysis, while significant dissimilarity supports more aggressive analysis. Additional factors may include rate acceleration, which, if present, supports the use of more aggressive analysis, correlation analysis (beat-to-beat or to a template), the presence of noise or overdetection. Another factor can be the presence of alternating patterns when observing a feature such as width, correlation, amplitude, frequency content or beat intervals across three or more detections, with the presence of alternating patterns supporting conservative criteria as these may suggest overdetection even if a positive declaration of overdetection is not made.

Based on the assessment of such factors, one of three routes is followed in the illustrative example of FIG. 8. If the predominant conclusion from assessing several factors supports conservative criteria, as indicated at 282, relatively more conservative criteria will be applied, as shown at 284. If there is no predominant conclusion and the factors considered split, at shown at 286, then a dynamic criteria based on prior episode history or clinical settings of the system is applied, as shown at 288. If the predominant conclusion from assessing several factors supports aggressive criteria as shown at 290, then relatively more aggressive criteria are applied as shown at 292.

The criteria selected at 284, 288 or 292 is then applied to making a decision, as shown at 294. The decision at 294 may be an episode decision, driving the initiation of data storage and/or heightened signal analysis, for example or, optionally, to begin therapy delivery or high voltage therapy preparation. In an alternative embodiment, the decision at 294 may instead be a decision to begin preparation for high voltage therapy delivery or a decision to begin low voltage therapy such as antitachycardia pacing, with episode decisions being made liberally in advance of the decision at 294.

At blocks 284 and 292, the illustration in FIG. 8 is stated in relative terms. By "More" Conservative criteria at 284, the example indicates that at least one arrhythmia analysis factor is modified so that at least one detected condition that would have met the arrhythmia criteria before modification will no longer meet the arrhythmia criteria. On the other side, at 292, the application of more aggressive criteria indicates that at least one arrhythmia analysis factor is modified so that at least one detected condition that would not have met the arrhythmia criteria before modification would now meet the arrhythmia criteria.

In a variant of FIG. 8, block 284 applies the most conservative criteria available, for example, if a system allows use of an X/Y counter set to 40/50 and that is the maximum X and Y available, then block 284 would apply the maximum X and Y. Likewise, in this variant, block 292 applies the most aggressive criteria available, for example, if the system allows the use of an X/Y counter set to 6/8 and that is the minimum X and Y available, then block 292 would apply the minimum X and Y.

Rather than the three branches shown in FIG. 8, another example applies a gradient as indicated at 296. In this example, the extent of modification of the applied criteria is proportional to the extent that the factors considered support one conclusion (aggressive) or the other (conservative). Bands for the assessment may be determined using the criteria noted above.

In a further example, the use of "dynamic" criteria is eliminated, and the factors existing upon identification of the potential arrhythmia 280 are used to select from a gradient of available adjustments to the decision criteria.

In another example, block 294 is a therapy decision block, where the criteria selected at 284/288/292 is applied. Episode declaration, in this example, is a predicate to the method and would be included as part of block 280. Thus, the episode or "preliminary declaration of arrhythmia" would occur first at or before block 280, with a subsequent selection of the therapy decision criteria occurring in a method as shown in FIG. 8. Once the therapy decision criteria are selected, the method would proceed to a therapy decision.

In some embodiments the indications used to select decision criteria may come from sources other than the electrical cardiac signal. For example, a blood pressure monitoring sensor may provide an indication of blood pressure to the system, with very low blood pressure supporting the use of more aggressive arrhythmia analysis criteria, and the absence of low blood pressure supporting the use of more conservative criteria. In another example, a cardiac motion sensor, such as a piezoresistor or piezoelectrical element may be placed in a blood vessel associated with the heart or placed epicardially or endocardially to monitor heart motion may provide an input, with overly rapid motion, or lack of motion, both supporting aggressive arrhythmia detection criteria. In another example, oximetry (or other blood constituent monitor) can be used to determine whether more aggressive criteria should apply, where low blood oxygenation would support use of more aggressive criteria, while normal blood oxygenation would support more conservative criteria. In yet another example, an accelerometer is provided and enabled to identify a sudden change in position (possibly indicating the patient has fallen), and the existence of data from the accelerometer suggesting a fall has occurred would be used to select the more aggressive criteria.

In another set of examples, an implantable defibrillator is enabled with the ability to detect RF signals in response to the identification of a potential arrhythmia. Upon receipt of RF signals generated in response to an identified treatable condition from one or more other implanted systems, the defibrillator would then select more aggressive arrhythmia detection criteria. For example, an implantable subcutaneous defibrillator may coexist with an implantable leadless pacemaker (see US Patent Application Pub. No. 20110208260, for example). The leadless pacemaker may identify through its detection methods that the cardiac rate is above a preset boundary, and would then begin transmitting an alarm using, for example, RF communication, sonic output, or by specially shaped pacing outputs. The subcutaneous ICD, upon identifying a potential arrhythmia, would begin observing whether any communication was being generated by the leadless pacemaker. Receipt or identification of such a communication would then lead the subcutaneous ICD to modify its detection parameters. This would allow the subcutaneous ICD to independently verify the arrhythmia, while still allowing the leadless pacemaker to play a roll. In another example, a pulse oximeter or blood pressure monitor would provide an output signal.

In another example, a blood constituent monitor or blood pressure monitor may be polled by the implantable device. For example, RFID circuitry would be integrated with a monitor for blood oxygenation or pressure, where the RFID output embeds a feature indicating the status of blood oxygenation or pressure. When the cardiac therapy system identifies a potential arrhythmia, it generates an output that polls the RFID device to determine whether the monitored oxygenation or pressure is in a range indicating a need for immediate therapy. If so, then more aggressive parameters would be applied.

A first example takes the form of an implantable cardiac stimulus device comprising electrodes coupled to operational circuitry for sensing cardiac activity and detecting events in the sensed cardiac activity and delivering therapy in response to identified conditions, in which the operational circuitry is configured to use one or more arrhythmia identification parameters which can be modified within predefined ranges. In this first example, the operational circuitry is configured to: establish a preliminary identification of a potentially treatable arrhythmia using a set of detected events; determine whether the set of detected events are varying in shape or consistent in shape using a predefined parameter; if the set of detected events is varying in shape, apply a first value for the arrhythmia detection parameter to assess whether the preliminary identification of a potentially treatable arrhythmia should be declared as an episode of treatable arrhythmia; and if the set of detected events is not varying in shape, apply a second value for the arrhythmia detection parameter to assess whether the preliminary identification of a potentially treatable arrhythmia should be declared as an episode of treatable arrhythmia; wherein the second value is different from the first value.

A second example incorporates the first example, wherein the operational circuitry is further configured to identify a nonsustained episode of potentially treatable arrhythmia and, in response thereto, modify the second value for the arrhythmia detection parameter, and set the first value for the arrhythmia detection parameter to a predefined default value for the modified arrhythmia detection parameter.

A third example takes the form of an implantable cardiac stimulus device comprising electrodes coupled to operational circuitry for sensing cardiac activity and detecting events in the cardiac activity, the operational circuitry further being configured to deliver therapy in response to identified conditions. In this third example, the operational circuitry is configured to: observe features of the cardiac signal for the set of detected events and using the observed features to select from at least: a first set of arrhythmia declaration parameters; and a second set of arrhythmia declaration parameters; wherein the first set of arrhythmia declaration parameters is different from the second set of arrhythmia declaration parameters such that, for at least set of detected data, analysis using the first set of arrhythmia declaration parameters would not declare a treatable arrhythmia while analysis using the second set of arrhythmia declaration parameters would declare at treatable arrhythmia, and analyze the sensed cardiac activity using the selected set of arrhythmia declaration parameters. In a variant of this third example, the operational circuitry may also be configured to establish a preliminary identification of a potentially treatable arrhythmia using a set of detected events prior to selecting from among the arrhythmia detection parameters.

A fourth example incorporates the third example, in which the operational circuitry is further configured to observe features of the cardiac signal for the set of detected events to select from the first and second sets of arrhythmia declaration parameters without observing cardiac rate information. Instead, the operational circuitry in this fourth example is configured to analyze other features. Some such other features are noted in the following examples.

A fifth example incorporates the third example, wherein the operational circuitry is further configured to observe features of the cardiac signal for the set of detected events by determining whether a monomorphic cardiac signal is occurring. A sixth example incorporates the fifth example, wherein the operational circuitry is further configured to select the first set of arrhythmia declaration parameters in response to determining that a monomorphic cardiac signal is occurring. A seventh example incorporates the fifth example, wherein the operational circuitry is further configured to select the second set of arrhythmia declaration parameters in response to determining that a monomorphic cardiac signal is not occurring.

An eighth example incorporates the third example, wherein the operational circuitry is configured to observe features of the cardiac signal for the set of detected events by determining whether intervals defined between the detected events in the set of detected events are stable. A ninth example incorporates the eighth example, wherein the operational circuitry is configured to select the first set of arrhythmia declaration parameters in response to determining that the intervals are stable. A tenth example incorporates the eighth example, wherein the operational circuitry is configured to select the second set of arrhythmia declaration parameters in response to determining that the intervals are not stable.

An eleventh example incorporates the third example, wherein the operational circuitry is further configured to analyze individual detected events in order to identify whether any detections occur due to noise; and the operational circuitry is configured such that the step of observing features of the cardiac signal for the set of detected events comprises determining whether one or more detections have been identified as noise. A twelfth example incorporates the eleventh example, wherein the operational circuitry is configured to select the first set of arrhythmia declaration parameters in response to determining that one or more detections have been identified as noise. A thirteenth example incorporates the eleventh example, wherein the operational circuitry is configured to select the second set of arrhythmia declaration parameters in response to determining that no detections have been identified as noise.

A fourteenth example incorporates the third example, wherein the operational circuitry is further configured to analyze individual detected events in order to identify whether any detections occur due to overdetection; and the operational circuitry is configured such that the step of observing features of the cardiac signal for the set of detected events comprises determining whether one or more detections have been identified as being overdetections. A fifteenth example incorporates the fourteenth example, wherein the operational circuitry is configured to select the first set of arrhythmia declaration parameters in response to determining that one or more detections have been identified as overdetections. A sixteenth example incorporates the fourteenth example, wherein the operational circuitry is configured to select the second set of arrhythmia declaration parameters in response to determining that no detections have been identified as overdetections.

A seventeenth example incorporates the third example, wherein the operational circuitry is configured to observe features of the cardiac signal for the set of detected events by determining whether a sudden onset of increase cardiac rate has occurred. An eighteenth example incorporates the seventeenth example, wherein the operational circuitry is configured to select the first set of arrhythmia declaration parameters in response to determining that no sudden onset of increased cardiac rate has occurred. A nineteenth example incorporates the seventeenth example, wherein the operational circuitry is configured to select the second set of arrhythmia declaration parameters in response to determining that a sudden onset of increased cardiac rate has occurred.

A twentieth example takes the form of a method of cardiac signal analysis in an implantable cardiac device, the implantable cardiac device comprising electrodes coupled to operational circuitry for sensing cardiac activity and performing cardiac signal analysis, the method comprising: establishing a preliminary identification of a potentially treatable arrhythmia using a set of detected events; observing features of the cardiac signal for the set of detected events and using the observed features to select from: a first set of arrhythmia declaration parameters; and a second set of arrhythmia declaration parameters; wherein the first set of arrhythmia declaration parameters is different from the second set of arrhythmia declaration parameters such that, for at least set of detected data, analysis using the first set of arrhythmia declaration parameters would not declare a treatable arrhythmia while analysis using the second set of arrhythmia declaration parameters would declare at treatable arrhythmia.

A twenty-first example takes the form of an implantable cardiac stimulus device comprising electrodes coupled to operational circuitry for sensing cardiac activity and detecting events in the sensed cardiac activity and delivering therapy in response to identified conditions, in which the operational circuitry is configured to use one or more arrhythmia identification parameters which can be modified within predefined ranges. In this twenty-first example, the operational circuitry comprises establishing means to establish a preliminary identification of a potentially treatable arrhythmia using a set of detected events; determining means to determine whether the set of detected events are varying in shape or consistent in shape using a predefined parameter; first value application means configured to, if the set of detected events is varying in shape, apply a first value for the arrhythmia detection parameter to assess whether the preliminary identification of a potentially treatable arrhythmia should be declared as an episode of potentially treatable arrhythmia; and second value application means configured to, if the set of detected events is not varying in shape, apply a second value for the arrhythmia detection parameter to assess whether the preliminary identification of a potentially treatable arrhythmia should be declared as an episode of potentially treatable arrhythmia; wherein the second value is different from the first value.

A twenty-second example takes the form of an implantable cardiac stimulus device comprising electrodes coupled to operational circuitry for sensing cardiac activity and detecting events in the cardiac activity, the operational circuitry further being configured to deliver therapy in response to identified conditions, in which the operational circuitry comprises: establishing means for establishing a preliminary identification of a potentially treatable arrhythmia using a set of detected events; observing means for observing features of the cardiac signal for the set of detected events and using the observed features to select from: a first set of arrhythmia declaration parameters; and a second set of arrhythmia declaration parameters; wherein the first set of arrhythmia declaration parameters is more conservative than the second set of arrhythmia declaration parameters such that, for at least set of detected data, analysis using the first set of arrhythmia declaration parameters would not declare a treatable arrhythmia while analysis using the second set of arrhythmia declaration parameters would declare at treatable arrhythmia.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37

C.F.R. .sctn. 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An implantable cardiac stimulus device comprising electrodes coupled to operational circuitry for sensing cardiac activity and detecting events in the cardiac activity, the operational circuitry further being configured to deliver therapy in response to identified conditions, wherein the operational circuitry is configured to:
observe features of a cardiac signal for a set of detected events and use the observed features to select from at least:
a) a first set of arrhythmia identification parameters;
b) a second set of arrhythmia identification parameters; and
c) a third set of arrhythmia identification parameters; and
use the selected set of arrhythmia identfication parameters to analyze the sensed cardiac activity;
wherein the first set of arrhythmia identification parameters is different from at least the second set of arrhythmia identification parameters; and
wherein the operational circuitry is configured to observe features of the cardiac signal for the set of detected events by determining whether the cardiac signal is polymorphic or monomorphic and, if a polymorphic cardiac signal is observed, to select the first set of arrhythmia identification parameters in order to reduce time to therapy in the presence of the polymorphic cardiac signal.

2. The implantable cardiac stimulus device of claim 1, wherein the operational circuitry is configured to select the first set of arrhythmia identification parameters in response to determining that the cardiac signal is polymorphic.

3. The implantable cardiac stimulus device of claim 1, wherein the operational circuitry is configured to determine if the cardiac signal is narrow or wide in response to determining that the cardiac signal is monomorphic.

4. The implantable cardiac stimulus device of claim 3, wherein the operational circuitry is configured to select the second set of arrhythmia identification parameters in response to determining that the cardiac signal is monomorphic and narrow.

5. The implantable cardiac stimulus device of claim 3, wherein the operational circuitry is configured to select the third set of arrhythmia identification parameters in response to determining that the cardiac signal is monomorphic and wide.

6. The implantable cardiac stimulus device of claim 1, wherein the first set of arrhythmia identification parameters includes applying a minimum persistence.

7. The implantable cardiac stimulus device of claim 1, wherein the second set of arrhythmia identification parameters includes applying a maximum persistence.

8. The implantable cardiac stimulus device of claim 1, wherein the third set of arrhythmia identification parameters includes applying a current persistence, the current persistence defined by the operational circuitry in response to prior unsustained episodes.

9. The implantable cardiac stimulus device of claim 1, wherein an arrhythmia episode has been declared prior to selecting the arrhythmia identification parameters.

10. The implantable cardiac stimulus device of claim 1, wherein a potential arrhythmia episode has been identified prior to selecting the arrhythmia identification parameters.

11. A method of cardiac signal analysis in an implantable cardiac device, the implantable cardiac device comprising electrodes coupled to operational circuitry for sensing cardiac activity and performing cardiac signal analysis, the method comprising:
observing features of the cardiac signal for a set of detected events and using the observed features to select from:
a) a first set of arrhythmia identification parameters;
b) a second set of arrhythmia identification parameters; and
c) a third set of arrhythmia identification parameters; and
using the selected set of arrhythmia identification parameters to analyze the sensed cardiac activity;
wherein the first set of arrhythmia identification parameters is different from at least the second set of arrhythmia identification parameters; and
wherein the operational circuitry is configured to observe features of the cardiac signal for the set of detected events by determining whether the cardiac signal is polymorphic or monomorphic, and, if a polymorphic cardiac signal is observed, to select the first set of arrhythmia identification parameters in order to reduce time to therapy in the presence of the polymorphic cardiac signal.

12. The method of claim 11, wherein the step of using the observed features to select from the first set of arrhythmia identification parameters, the second set of arrhythmia identification parameters, and the third set of arrhythmia identification parameters is performed by selecting the first set of arrhythmia identification parameters in response to determining that the cardiac signal is polymorphic.

13. The method of claim 11, wherein the operational circuitry is configured to observe features of the cardiac signal for the set of detected events by determining whether the cardiac signal is narrow or wide in response to determining that the cardiac signal is monomorphic.

14. The method of claim 13, wherein the step of using the observed features to select from the first set of arrhythmia identification parameters, the second set of arrhythmia identification parameters, and the third set of arrhythmia identification parameters is performed by selecting the second set of arrhythmia identification parameters in response to determining that the cardiac signal is monomorphic and narrow.

15. The method of claim 13, wherein the step of using the observed features to select from the first set of arrhythmia identification parameters, the second set of arrhythmia identification parameters, and the third set of arrhythmia identification parameters is performed by selecting the third set of arrhythmia identification parameters in response to determining that the cardiac signal is monomorphic and wide.

16. The method of claim 11, wherein the first set of arrhythmia identification parameters includes applying a minimum persistence.

17. The method of claim 11, wherein the second set of arrhythmia identification parameters includes applying a maximum persistence.

18. The method of claim 11, wherein the third set of arrhythmia identification parameters includes applying a current persistence, the current persistence defined by the operational circuitry in response to prior unsustained episodes.

19. An implantable cardiac stimulus device comprising electrodes coupled to operational circuitry for sensing cardiac activity and detecting events in the cardiac activity, the operational circuitry further being configured to deliver therapy in response to identified conditions, wherein the operational circuitry is configured to:
 observe features of a cardiac signal for a set of detected events and use the observed features to select from at least:
  a) a first set of arrhythmia identification parameters;
  b) a second set of arrhythmia identification parameters; and
  c) a third set of arrhythmia identification parameters; and
 use the selected set of arrhythmia identification parameters to analyze the sensed cardiac activity;
 wherein the first set of arrhythmia identification parameters is different from at least the second set of arrhythmia identification parameters;
 wherein the operational circuitry is configured to observe features of the cardiac signal for the set of detected events by determining whether the cardiac signal is polymorphic or monomorphic; and
 wherein if the cardiac signal is polymorphic, the operation circuitry is configured to select the first set of arrhythmia identification parameter to reduce time to therapy if a polymorphic signal is identified, and if the cardiac signal is monomorphic, the operation circuitry is configured to select one of the second or third sets of arrhythmia identification parameters.

20. The implantable cardiac stimulus device of claim 19, wherein:
 the operational circuitry is configured to determine if the cardiac signal is narrow or wide in response to determining that the cardiac signal is monomorphic;
 the operational circuitry is configured to select the second set of arrhythmia identification parameters in response to determining that the cardiac signal is monomorphic and narrow; and
 the operational circuitry is configured to select the third set of arrhythmia identification parameters in response to determining that the cardiac signal is monomorphic and wide.

* * * * *